(12) United States Patent
Doguchi et al.

(10) Patent No.: US 7,573,499 B2
(45) Date of Patent: Aug. 11, 2009

(54) ENDOSCOPE APPARATUS FOR OBTAINING PROPERLY DIMMED OBSERVATION IMAGES

(75) Inventors: Nobuyuki Doguchi, Hino (JP); Yoshinori Takahashi, Hachioji (JP); Fumiyuki Okawa, Hino (JP); Katsuichi Imaizumi, Hachioji (JP); Takeshi Ozawa, Sagamihara (JP); Isami Hirao, Hachioji (JP); Sakae Takehana, Sagamihara (JP)

(73) Assignee: Olympus Corporation, Tokyo (JP)

( * ) Notice: Subject to any disclaimer, the term of this patent is extended or adjusted under 35 U.S.C. 154(b) by 917 days.

(21) Appl. No.: 10/873,951

(22) Filed: Jun. 22, 2004

(65) Prior Publication Data

US 2004/0257438 A1   Dec. 23, 2004

(30) Foreign Application Priority Data

Jun. 23, 2003   (JP) ............................. 2003-178652

(51) Int. Cl.
   A62B 1/04   (2006.01)
   A61B 1/04   (2006.01)
(52) U.S. Cl. .......................................... 348/65; 348/69
(58) Field of Classification Search ................... 348/45, 348/65–70
   See application file for complete search history.

(56) References Cited

U.S. PATENT DOCUMENTS

| | | | |
|---|---|---|---|
| 4,803,550 A | 2/1989 | Yabe et al. | |
| 4,967,269 A | 10/1990 | Sasagawa et al. | |
| 5,337,340 A | 8/1994 | Hynecek | |
| 6,080,104 A | 6/2000 | Ozawa et al. | |
| 6,689,050 B1 * | 2/2004 | Beutter et al. ................ | 600/117 |
| 7,037,259 B2 * | 5/2006 | Hakamata et al. ........... | 600/178 |
| 7,102,680 B2 * | 9/2006 | Mori et al. .................... | 348/314 |
| 7,209,162 B2 * | 4/2007 | Ota et al. ....................... | 348/68 |
| 7,312,823 B1 * | 12/2007 | Mori ............................. | 348/269 |

FOREIGN PATENT DOCUMENTS

| | | |
|---|---|---|
| EP | 1 099 405 A1 | 5/2001 |
| EP | 1 294 186 A2 | 3/2003 |
| JP | 2001-29313 | 2/2001 |
| JP | 2003-079570 | 3/2003 |

* cited by examiner

Primary Examiner—David Czekaj
(74) Attorney, Agent, or Firm—Scully, Scott, Murphy & Presser, P.C.

(57) ABSTRACT

A CCD driver circuit adjusts and supplies pulse-type signals to a CCD in order to adjust the sensitivity of the CCD. A metering circuit meters a signal output from the CCD. A sensitivity control circuit controls the sensitivity of the CCD by controlling the sensitivity multiplication factor of the CCD based on a metering result by the metering circuit. A metering correcting circuit corrects a metering result from the metering circuit based on a charge multiplication factor from the sensitivity control circuit. An aperture control circuit controls an aperture based on a metering signal corrected by the metering correcting circuit. Thus, an image of an object of which strength of light largely varies can be obtained as an image under a proper dimming state.

10 Claims, 19 Drawing Sheets

ENDOSCOPE APPARATUS FOR OBTAINING PROPERLY DIMMED OBSERVATION IMAGES

This application claims benefit of Japanese Application No. 2003-178652 filed in Japan on Jun. 23, 2003, the contents of which are incorporated by this reference.

BACKGROUND OF THE INVENTION

1. Field of the Invention

The present invention relates to an endoscope apparatus for obtaining an image by means of an image pickup element for picking up images of an object by integrating charges.

2. Description of the Related Art

Conventionally, an endoscope apparatus includes an endoscope such as an electronic endoscope having a solid image pickup element, a processor, a light source apparatus and a monitor in general. In the conventional endoscope apparatus, an insert portion of the endoscope is inserted into a body cavity. Here, light is irradiated from the light source apparatus to an object through a light guide contained in the endoscope and is reflected from the object. The solid image pickup element provided at the distal end of the endoscope optoelectronically converts the reflected light. Then, the processor signal-processes the output signals resulting from the optoelectronic conversion, and the signals are displayed on the monitor.

Recently, a technology has been used for irradiating an exciting light to a part to be observed of a living-body tissue, imaging auto fluorescence occurring from the living-body tissue from the exciting light or photodynamic diagnosis (PDD) using fluorescence drugs called photosensitizers as a two-dimensional image, and diagnosing a lesion (such as a type of disease and an invasive range) of a cancer, for example, based on the fluorescent image. Florescent observation apparatuses for performing fluorescent observation have been developed.

Regarding auto fluorescence, when exciting light is irradiated to a living-body tissue, fluorescence is generated by the exciting light at the longer wavelength side than that of the exciting light. A fluorescent material in a living body may be nicotin amide adenine dinucleotides (NADH), Flavin mono nucleotide (FMN) or collagen and the like. Recently, the correlation between a biological endogenous compound generating such fluorescence and a disease is being clarified, and a cancer, for example, can be diagnosed by observing the fluorescence.

Regarding PDD, HpD(hematoporphyrin), Photofrin or ALA(δ-amino levulinicacid) and the like may be used as a fluorescent material to be injected into a living body. These photosensitizers can be uniquely accumulated onto a cancer, for example, and a lesion can be diagnosed by injecting these photosensitizers into a body and observing fluorescence. Alternatively, a fluorescent material may be added to monoclonal antibiotics, so that a fluorescent material can be accumulated in a lesion through an antigen-antibody reaction.

For example, the fluorescence observing apparatus may adjust and control the sensitivity of a CCD type solid image pickup element provided at the distal end of an endoscope so as to achieve a constant screen average of fluorescent images, that is, to achieve a constant intensity average of a monitor.

In order to image weak fluorescence by using the fluorescence observing apparatus, an aperture in the light source is fully opened, and the sensitivity of a charge-multiplying solid image pickup element having adjustable sensitivity is multiplied. Then, the sensitivity of the charge-multiplying solid image pickup element is further automatically gain-controlled so that a fluorescent image can be obtained.

SUMMARY OF THE INVENTION

According to one aspect of the invention, there is provided an endoscope apparatus including an endoscope having an image pickup element having a sensitivity, which can be changed by multiplying generated charges by supplied pulse-type signals, a light source portion for irradiating light to an object, an aperture portion for adjusting an amount of light to be irradiated to the object, a driver portion for adjusting and supplying the pulse-type signals to the image pickup element in order to change the sensitivity of the image pickup element, a metering portion for generating an intensity signal based on a signal output from the image pickup element, a sensitivity control portion for, based on the intensity signal of the metering portion, supplying to the driver portion a sensitivity control signal for generating the pulse-type signals for controlling a charge multiplication factor of the image pickup element, a metering correcting portion for correcting the intensity signal by the metering portion based on the charge multiplication factor, and an aperture control portion for controlling the aperture portion based on a metering signal corrected by the metering correcting portion.

The other features and advantages of the present invention will be adequately apparent from descriptions below.

BRIEF DESCRIPTION OF THE DRAWINGS

FIG. 1 is a block diagram showing a schematic configuration of an endoscope apparatus;

FIG. 2 is a block diagram of a CCD;

FIG. 3A is a timing chart of a sensitivity control pulse φCMD of the CCD;

FIG. 3B is a timing chart of a horizontal transfer pulse φS1 of the CCD;

FIG. 3C is a timing chart of a horizontal transfer pulse φS2 of the CCD;

FIG. 4 is a graph showing a relationship between voltage to be applied to a charge multiplying detector and a sensitivity multiplication factor with respect to a CCD sensitivity;

FIG. 5A is a timing chart of an operation of a rotating filter in a normal light mode;

FIG. 5B is a timing chart of vertical transfer pulses φP1 and φP2 in the normal light mode;

FIG. 5C is a timing chart of horizontal transfer pulses φP1 and φP2 in the normal light mode;

FIG. 5D is a timing chart of a sensitivity control pulse φCMD in the normal light mode;

FIG. 5E is a timing chart of a signal output from the CCD in the normal light mode;

FIG. 5F is a timing chart of an operation of the rotating filter in a special light mode;

FIG. 5G is a timing chart of vertical transfer pulses φP1 and φP2 in the special light mode;

FIG. 5H is a timing chart of horizontal transfer pulses φP1 and φP2 in the special light mode;

FIG. 5I is a timing chart of a sensitivity control pulse φCMD in the special light mode.

FIG. 5J is a timing chart of a signal output from the CCD in the special light mode;

FIG. 6 is a block diagram showing a configuration of a metering circuit in FIG. 1;

FIG. 7 is a block diagram showing a configuration of a sensitivity control circuit in FIG. 1;

FIG. 8 is a block diagram showing a configuration of a metering correcting circuit in FIG. 1;

FIG. 9 is a plan view showing a configuration of a rotating filter;

FIG. 10 is a graph showing a CCD sensitivity characteristic (monitor output signal);

FIG. 11 is a graph showing a CCD sensitivity characteristic (S/N characteristic);

FIG. 12 is a graph showing a spectral characteristic of a light source apparatus during an observation with special light (fluorescence observation); and FIG. 13 is a graph showing a spectral characteristic of fluorescence and reflected light during an observation with special light (fluorescence observation).

FIG. 14 is a block diagram showing a schematic configuration of an endoscope apparatus; and FIG. 15 is a block diagram showing a configuration of a sensitivity control circuit in FIG. 14.

FIG. 16 is a block diagram showing a schematic configuration of an endoscope apparatus;

FIG. 17A is a timing chart of an operation of a rotating filter;

FIG. 17B is a timing chart of vertical transfer pulses $\phi P1$ and $\phi P2$;

FIG. 17C is a timing chart of a sensitivity control pulse $\phi CMD$ in the special light mode;

FIG. 17D is a timing chart of horizontal transfer pulses $\phi S1$ and $\phi S2$;

FIG. 17E is a timing chart of a signal output from the CCD;

FIG. 18 is a graph showing a spectral characteristic of a light source apparatus during an observation with narrow band light;

FIG. 19 is a graph showing a spectral characteristic of reflected light during an observation with narrow band light;

FIG. 20 is a graph showing a CCD sensitivity characteristic (monitor output signal); and FIG. 21 is a graph showing a CCD sensitivity characteristic (S/N characteristic).

FIG. 22 is a block diagram showing a schematic configuration of an endoscope apparatus; and FIG. 23 is a block diagram showing a configuration of a sensitivity control circuit in FIG. 22.

DETAILED DESCRIPTION OF THE PREFERRED EMBODIMENTS

First Embodiment

[Construction]

Figure 1:
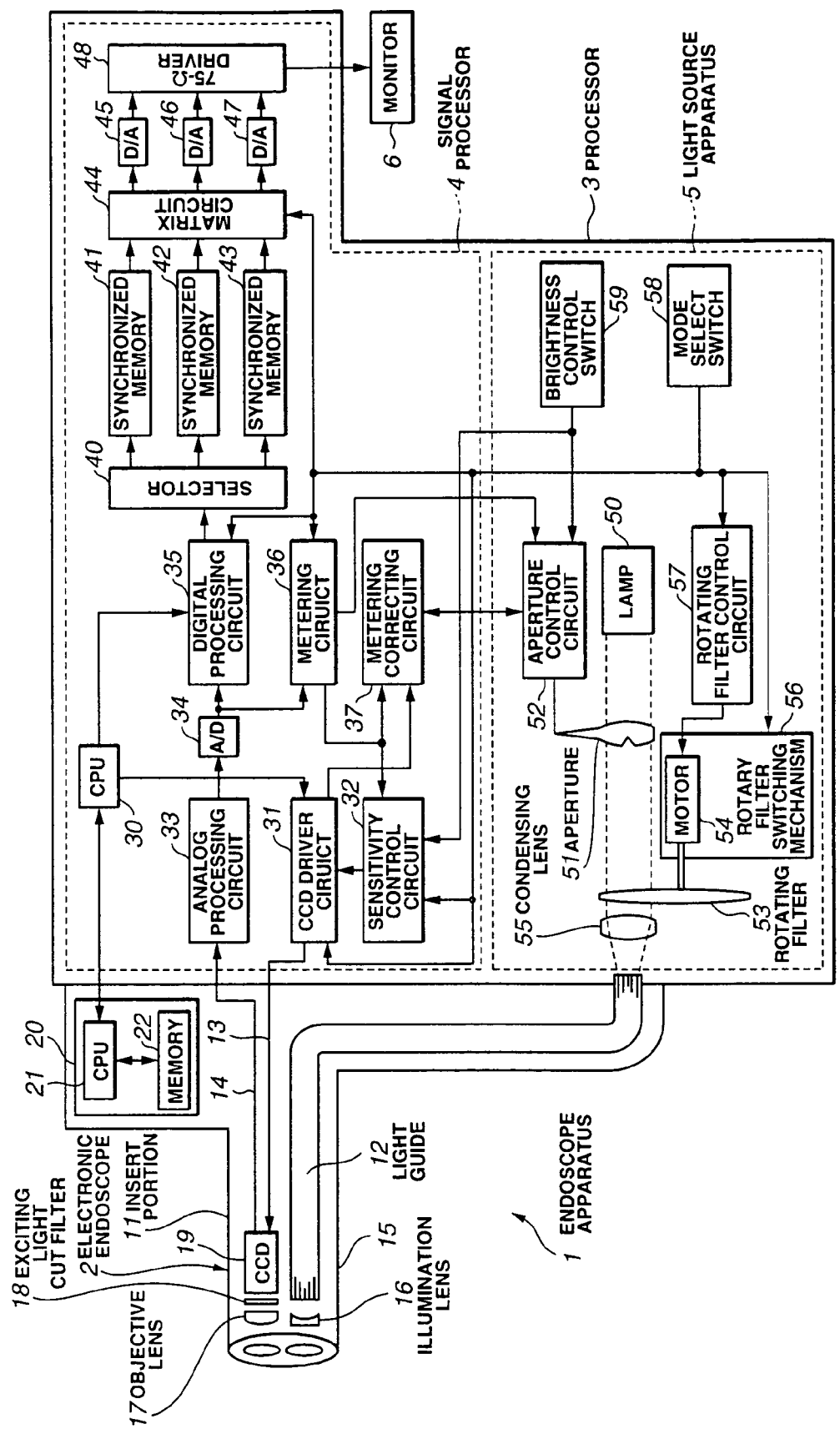
FIGS. 1 to 13 relate to a first embodiment of the present invention.

As shown in FIG. 1, an endoscope apparatus 1 according to a first embodiment includes an electronic endoscope (called endoscope hereinafter) 2, a processor 3 and a monitor 6.

The endoscope 2 contains a CCD 19 at an endoscope distal end 15 of the endoscope 2.

The endoscope 2 is removably connected to the processor 3. The processor 3 contains a signal processor 4 and a light source apparatus 5. The light source apparatus 5 may be provided separately from the processor 3.

The monitor 6 is connected to the processor 3 and displays video signals image-processed in the processor 3.

Next, the endoscope 2 will be described in detail.

The endoscope 2 has a long and narrow insert portion 11 to be inserted into a patient's body cavity.

Here, the insert portion 11 includes a soft part for the digestive tract, the bronchi, the neck (the pharynx) and the bladder and a hard part for the abdominal cavity, the thorax and the womb.

A light guide 12, CCD drive signal lines 13 and CCD output signal lines 14 are provided in the insert portion 11.

The distal end of the light guide 12, an illumination lens 16, an objective lens 17, an exciting light cut filter 18 and a CCD 19 are provided in the distal end 15 of the insert portion 11.

The light guide 12 guides illumination light from the light source apparatus 5 provided in the processor 3 to the distal end 15 of the insert portion 11.

The illumination lens 16 is mounted at the distal end 15 of the insert portion 11 and is provided closely to the distal end surface of the light guide 12.

The illumination light guided from the light source apparatus 5 by the light guide 12 is irradiated to an object through the illumination lens 16.

The objective lens 17 forms an image from light from an object.

The exciting light cut filter 18 is mounted in front of the CCD 19 and allows only the beams in a specific wavelength band to pass through. According to this embodiment, the exciting light cut filter 18 has a spectral characteristic allowing auto fluorescence (with a wavelength equal to or higher than about 500 nm) caused from a living-body tissue to pass through and not allowing exciting light (with a wavelength equal to or lower than about 470 nm) to pass through.

The reflected light and auto fluorescence from an object form an image on the light receptive surface of the CCD 19 through the objective lens 17 and exciting light cut filter 18.

The CCD 19 is an image sensor provided at the distal end 15 of the insert portion 11 and provided at an image-forming position of the objective lens 17. In FIG. 1, the CCD 19 is disposed in a direct-view form but may be disposed in a perspective- or elevation-view form.

The CCD 19 is connected to a CCD driver circuit 31 of the signal processor 4 within the processor 3 through the multiple drive signal lines 13. The CCD 19 controls an electronic shutter, integrates signal charges, controls and reads sensitivity by using drive signals generated by the CCD driver circuit 31.

An object image formed on the light receptive surface of the CCD 19 by the objective lens 17 and the exciting light cut filter 18 is transferred and output from a floating diffusion amplifier after optoelectronic conversion at each pixel of the CCD 19. Signals output from the CCD 19 are supplied to an analog processing circuit 33 of the signal processor 4 within the processor 3 through the multiple CCD output signal lines 14.

The endoscope 2 has a storage device 20 close to the proximal end. The storage device 20 includes a CPU 21 and a memory 22.

The memory 22 as storage means may be a non-volatile EEPROM and stores data such as a sensitivity multiplication factor characteristic of the CCD 19.

The CPU 21 controls reading and writing of data from/to the memory 22 and controls exchanges (communication) of data with the processor 3.

The memory 22 stores data relating to the endoscope, which will be described below, as well as data of the sensitivity multiplication factor characteristic of the CCD 19.

The data to be stored in this case may be a type name of the endoscope 2, a serial number of the endoscope 1, white-balance set values (that is, multiple values for normal light and special light), information of a forceps channel of the endoscope 2, the outer diameter data of the distal end 15 of the endoscope 2 and/or the outer diameter data of the insert portion 11 of the endoscope 2.

According to this embodiment, the signal processor 4 has a CPU 30, a CCD driver circuit 31, a sensitivity control circuit 32, an analog processing circuit 33, an analog/digital converter (called A/D converter hereinafter) 34, a digital processing circuit 35, a metering circuit 36, a metering correcting circuit 37, a selector 40, simultaneous memories 41, 42 and 43, a matrix circuit 44, digital/analog converters (called D/A converter hereinafter) 45, 46 and 47 and a 75-Ω driver 48.

The light source apparatus 5 has a lamp 50, an aperture 51, an aperture control circuit 52, a rotating filter 53, a motor 54, a condensing lens 55, a rotating filter switching mechanism 56, a rotating filter control circuit 57, a mode select switch 58, and a brightness control switch 59.

When the endoscope 2 is connected to the processor 3, the CPU 30 reads and controls different kinds of data stored in the memory 22 through the CPU 21. In this case, the different kinds of data stored in the memory 22 are output to the CPU 30 through the CPU 21, and the CPU 30 reads the different kinds of data.

The CPU 30 outputs to the CCD driver circuit 31 sensitivity multiplication factor characteristic data of the CCD 19 obtained from the memory 22.

The CPU 30 further outputs to the digital processing circuit 35 the type name, serial number and white-balance set values of the endoscope 2, for example.

Next, the CCD 19 will be described in detail.

According to this embodiment, the CCD 19 may be a solid image pickup element having an adjustable sensitivity by using an ionizing phenomenon as disclosed in U.S. Pat. No. 5,337,340, "Charge Multiplying Detector (CMD) suitable for small pixel CCD image sensors".

The CCD 19 has a charge multiplying detector between a horizontal transfer register and a floating diffusion amplifier within the CCD 19 or in each pixel. By applying pulses in a high electric field from the processor 3 to the charge multiplying detector so that signal charges can obtain energy from a high electric field and can collide with electrons in a valence band. Thus, new charges (secondary electrons) are generated by the ionization.

For example, by using an avalanche effect, the application of pulses causes the generation of secondary electrons in a chain-reaction manner. On the other hand, by using an ionization, a pair of electron-hole is only generated by the application of pulses at a lower voltage than that of the avalanche effect.

When the CCD 19 has the charge multiplying detector before the floating diffusion amplifier, the number of signal charges can be arbitrarily multiplied by controlling a voltage value (multiplicity) of pulses to be applied or the number of pulses.

On the other hand, when the charge multiplying detector is provided in each pixel, the number of signal charges can be arbitrarily multiplied by controlling a voltage value (multiplicity) of pulses to be applied or the number of pulses.

Figure 2:
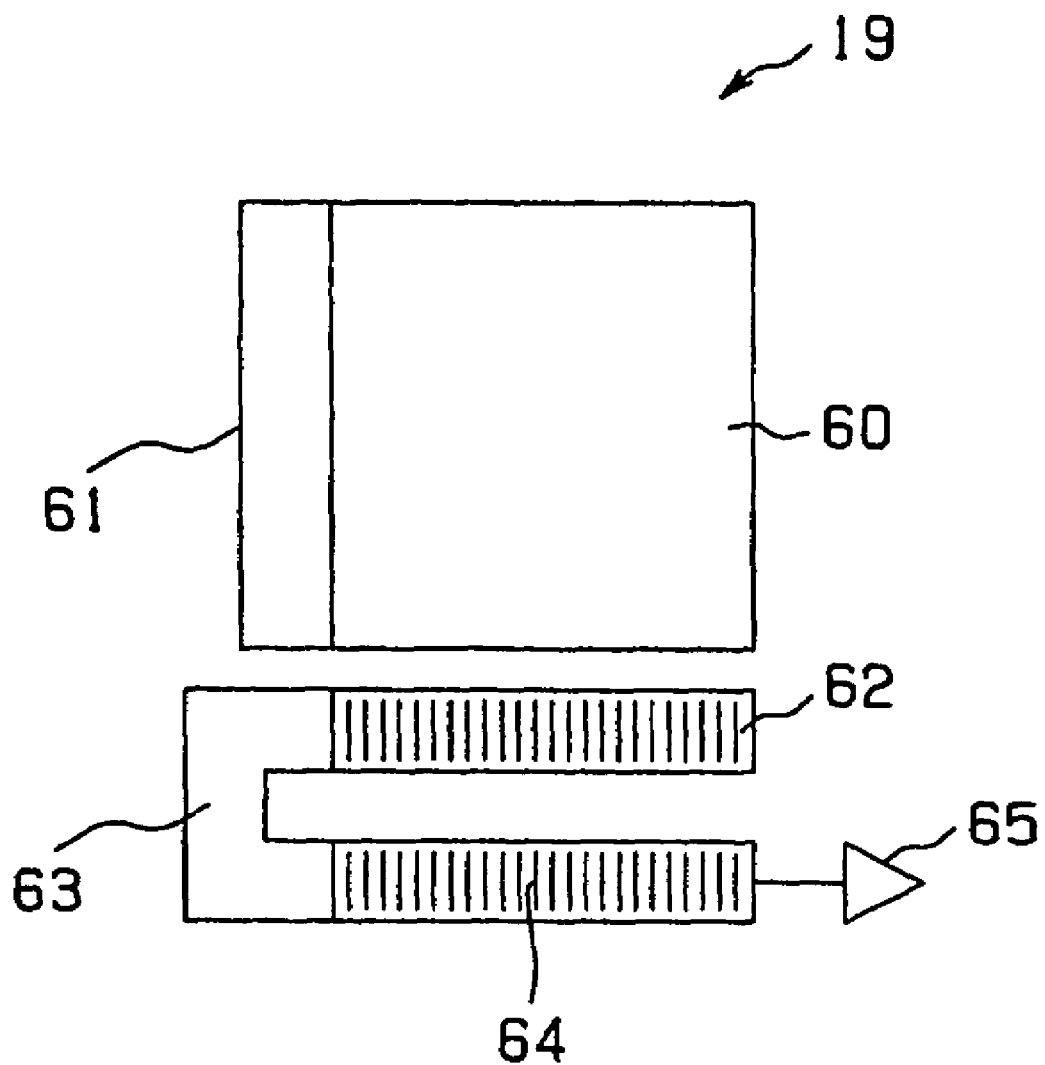

According to this embodiment, the CCD 19 is a Full Frame Transfer (FFT) type monochrome CCD having a charge multiplying detector between a horizontal transfer register and a floating diffusion amplifier, as shown in FIG. 2.

The CCD 19 has an image area 60 and optical black (OB) portion 61 as a light-receiving portion, a horizontal transfer register 62, a dummy 63, a charge multiplying detector 64 and a floating diffusion amplifier 65. The charge multiplying detector 64 includes cells the number of which is substantially equal to or two times of the number of cells of the horizontal transfer register 62.

The CCD 19 may be of frame transfer (FT) type having a charge integrating portion.

The signal charges generated at pixels of the image area 60 are transferred to the horizontal transfer register 62 for each one horizontal line by vertical transfer pulses $\phi P1$ and $\phi P2$ and are transferred from the horizontal transfer register 62 to the dummy 63 and the charge multiplying detector 64 by the horizontal transfer pulses $\phi S1$ and $\phi S2$. Then, a sensitivity control pulse $\phi CMD$ is applied to each cell of the charge multiplying detector 64 having multiple cells so that a charge can be transferred to each of the cells, can be sequentially multiplied in a stepwise manner and can be sequentially transferred to the floating diffusion amplifier 65. The floating diffusion amplifier 65 converts and outputs charges from the charge multiplying detector 64.

Figure 3:
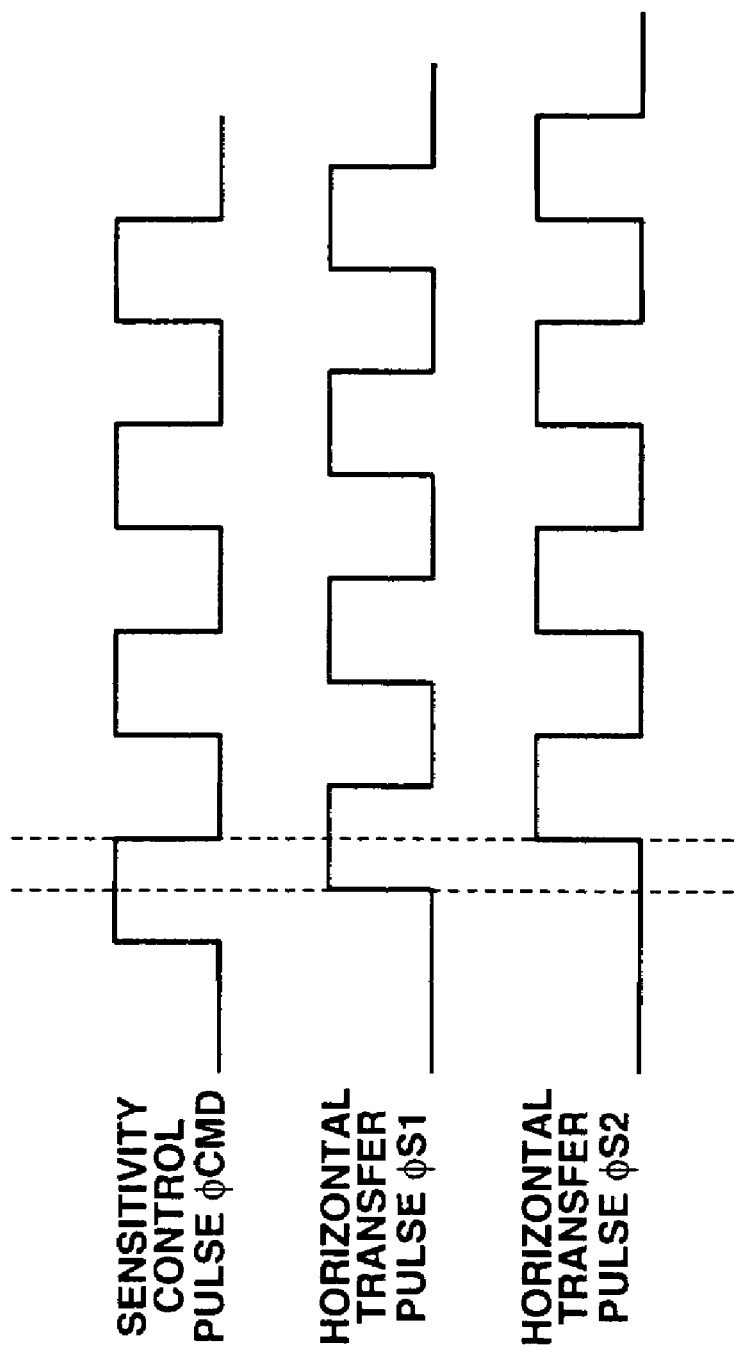

As shown in phases of the sensitivity control pulse $\phi CMD$ and the horizontal transfer pulses $\phi S1$ and $\phi S2$ in FIGS. 3A to 3C, the sensitivity control pulse $\phi CMD$ rises before the horizontal transfer pulse $\phi S1$ rises while the sensitivity control pulse $\phi CMD$ drops before the horizontal transfer pulse $\phi S1$ drops.

Figure 4:
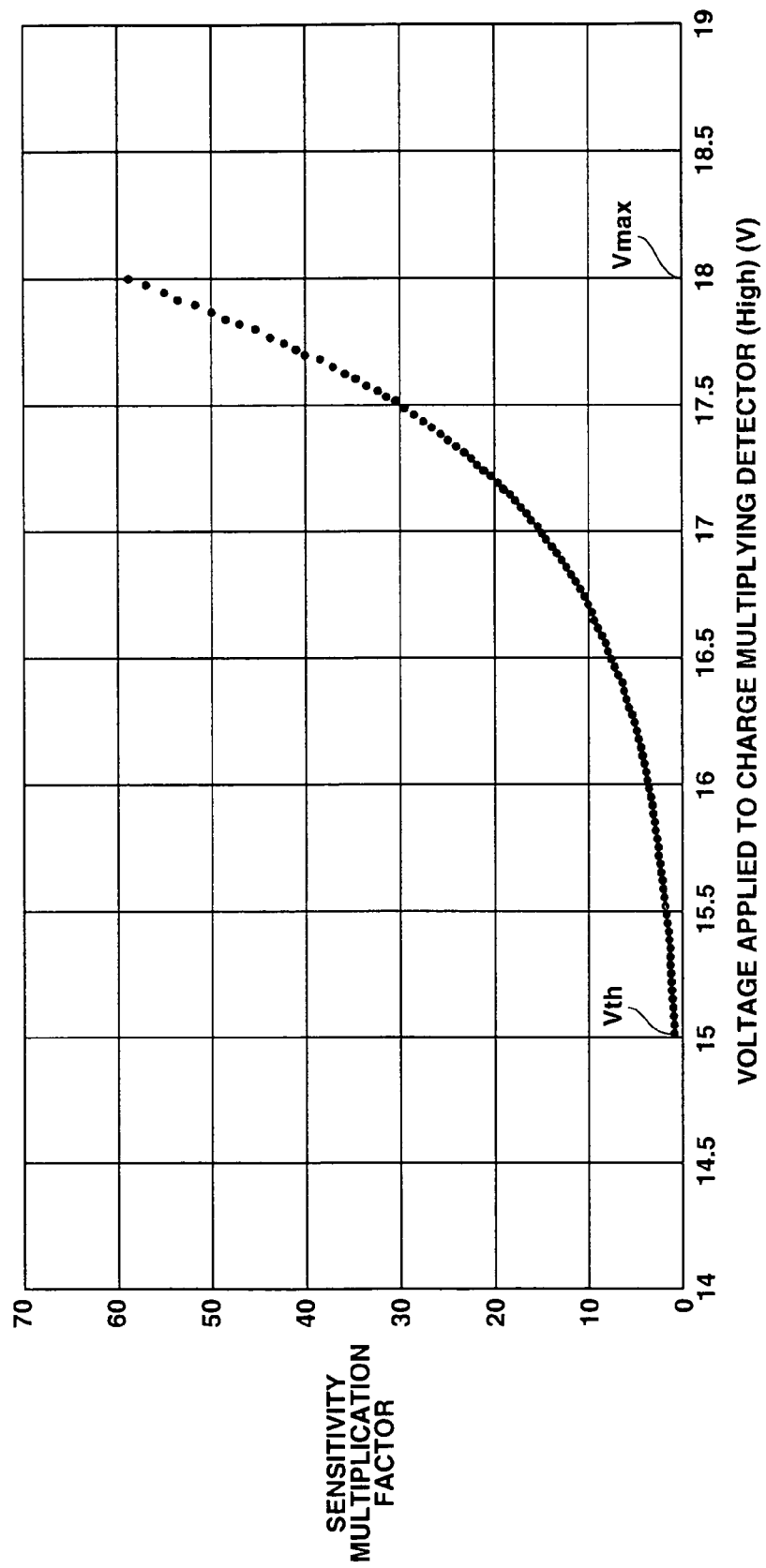

The sensitivity multiplication factor obtained by the charge multiplying detector 64 can be adjusted by changing the magnitude of a voltage value (multiplicity) of the sensitivity control pulse $\phi CMD$ from the CCD driver circuit 31 to the charge multiplying detector 64. Multiplication is performed stage by stage at each cell in the charge multiplying detector 64. As shown in FIG. 4, the sensitivity multiplication factor obtained by the charge multiplying detector 64 has a characteristic that, when applied voltage exceeds a threshold value Vth, the charge multiplication starts and the sensitivity is multiplied exponentially.

When the sensitivity control pulse $\phi CMD$ is 0 V to the threshold value Vth, signal charges are only transferred by the charge multiplying detector 64 without charge multiplication. The threshold value for starting charge multiplication and the steepness degree of the sensitivity multiplication factor with respect to applied voltage depend on a CCD parameter and is adjustable in design.

FIGS. 5A to 5J are timing charts of drive signals and output signals of the CCD 19 in a normal light mode and in a special light (fluorescence observation) mode-. FIG. 5A illustrates an operation of the rotating filter 53 in a normal light mode. FIG. 5B shows vertical transfer pulses $\phi P1$ and $\phi P2$ in the normal light mode. FIG. 5C shows horizontal transfer pulses $\phi S1$ and $\phi S2$ in the normal light mode. FIG. 5D shows a sensitivity control pulse $\phi CMD$ in the normal light mode. FIG. 5E shows a signal output from the CCD 19 in the normal light mode. FIG. 5F illustrates an operation of the rotating filter 53 in a special light mode. FIG. 5G shows vertical transfer pulses $\phi P1$ and $\phi P2$ in the special light mode. FIG. 5H shows horizontal transfer pulses $\phi S1$ and $\phi S2$ in the special light mode. FIG. 5I shows a sensitivity control pulse $\phi CMD$ in the special light mode. FIG. 5J shows a signal output from the CCD 19 in the special light mode.

As shown in FIGS. 5A to 5J, the CCD driver circuit 31 outputs vertical transfer pulses $\phi P1$ and $\phi P2$, horizontal transfer pulses $\phi S1$ and $\phi S2$ and an electronic shutter pulse $\phi OFD$ (not shown) as drive signals to the CCD 19 in the normal light mode and in the special light (fluorescence observation) mode.

The CCD 31 does not output a sensitivity control pulse φCMD to be supplied to the CCD 19 in the normal light mode but outputs a sensitivity control pulse φCMD to the CCD 19 in the special light (fluorescence observation) mode. When a sensitivity control pulse φCMD is output in the normal light mode, the voltage value may be equal to or lower than the threshold value Vth.

In the normal light mode, incident light from an object to the light receptive surface of the CCD 19 during R, G and B exposure periods shown in FIG. 5A is optoelectronically converted so as to be integrated as signal charges.

In a light-shield period shown in FIG. 5A, the CCD driver circuit 31 outputs vertical transfer pulses φP1 and φP2 shown in FIG. 5B and horizontal transfer pulses φS1 and φS2 shown in FIG. 5C. Thus, the CCD 19 reads signals, and the signals shown in FIG. 5E are output from the CCD 19.

Here, as described above, the CCD driver circuit 31 does not output a sensitivity control pulse φCMD in the normal light mode.

Thus, in the normal light mode, the charge multiplying detector 64 does not perform charge multiplication, and the sensitivity multiplication factor is 1 (without multiplication).

In the special light mode, the CCD 19 optoelectronically converts incident light from an object to the light receptive plane of the CCD 19 during exposure periods with three wavelengths Ex1, Ex2 and Ex3 shown in FIG. 5F so as to be integrated as signal charges.

In a light-shield period shown in FIG. 5F, that is, in a reading period of the CCD 19, the CCD driver circuit 31 outputs vertical transfer pulses φP1 and φP2 shown in FIG. 5G, horizontal transfer pulses φS1 and φS2 shown in FIG. 5H and a sensitivity control pulse φCMD shown in FIG. 5I. Thus, the CCD 19 reads the signals, and the signals shown in FIG. 5J are output from the CCD 19.

Here, the CCD driver circuit 31 adjusts a voltage value (multiplicity) of the sensitivity control pulse φCMD shown in FIG. 5I based on data supplied from the sensitivity control circuit 32. The CCD driver circuit 31 outputs the sensitivity control pulse φCMD shown in FIG. 5I to the CCD 19 in a phase relationship in synchronization with the horizontal transfer pulses φS1 and φS2 shown in FIG. 5H.

Thus, in the special light mode, the CCD driver circuit 31 controls CCD 19 so as to obtain a desired sensitivity multiplication factor by changing a voltage value (multiplicity) of the sensitivity control pulse φCMD applied to the charge multiplying detector 64.

In this way, charges are integrated at each pixel of the image area 60 of the CCD 19 during a light exposure period while a drive signal is output to the CCD 19 during a light-shield period. Charges at each pixel are sequentially transferred to the horizontal transfer register 62 by vertical transfer pulses φP1 and φP2 for each one horizontal line, are sequentially transferred to the dummy 63, the charge multiplying detector 64 and the floating diffusion amplifier 65 by the horizontal transfer pulses φS1 and φS2, are converted to voltage in the floating diffusion amplifier 65 and are output as voltage signals.

The light-exposure period of the CCD 19 depends on the type of the special light mode. According to this embodiment, the light-exposure time (integrating time) in the fluorescence observation mode is three times of that of the normal light mode.

In the CCD 19, driving timing and reading timing are switched in accordance with an observation mode (mode select signal) selected via the mode select switch 58.

A counter value relating to a voltage value (multiplicity) of a sensitivity control pulse φCMD to be output to the charge multiplying detector 64 is input from the sensitivity control circuit 32 to the CCD driver circuit 31. Data of a sensitivity multiplication factor characteristic (relationship between applied voltage and sensitivity multiplication factor) of the charge multiplying detector 64 of the CCD 19 is input from the memory 22 of the storage device 20 to the CCD driver circuit 31 through the CPU 21 and the CPU 30.

A correspondence relationship between a counter value and a value of voltage to be applied to the charge multiplying detector 64 is defined so as to be a voltage Vth shown in FIG. 4 when the counter value is minimum and be a voltage Vmax shown in FIG. 4 when the counter value is maximum. The sensitivity control pulse φCMD corresponding to the counter value from the sensitivity control circuit 32 is output in the range from Vth to Vmax to the charge multiplying detector 64. Since the sensitivity multiplication factor characteristic differs among CCDs and/or varies due to a variation in drive signal lines, the sensitivity control circuit 32 has correcting means for matching the minimum value Vth and maximum value Vmax of voltage of the sensitivity control pulse φCMD with the minimum value and maximum value of the counter value.

A relationship between a voltage value of the sensitivity control pulse ΦCMD and a sensitivity multiplication factor of the charge multiplying detector 64 shown in FIG. 2 is represented by EQ1 below:

$$M(V) = C \cdot \text{Exp}\{\alpha(V - V\text{th})\} \quad [EQ1]$$

where M(V) is a sensitivity multiplication factor when a voltage value (multiplicity) of a sensitivity control pulse ΦCMD is V(v), Vth is a threshold value for starting a charge multiplication, and C, α and Vth are unique constants of the device.

For example, when a value of voltage to be applied to the charge multiplying detector 64 is V(V), the counter value may vary by ±1. Then, the applied voltage V'=V±ΔV(V) is obtained where a voltage value having the variation in counter value equivalent to 1 is ΔV(V). Therefore, the sensitivity multiplication factor here is represented by EQ2 below:

$$M(V') = C \cdot \text{Exp}\{\alpha(V' - V\text{th})\} \quad [EQ2]$$
$$= C \cdot \text{Exp}\{\alpha(V \pm \Delta V - V\text{th})\}$$

The variation rate of the sensitivity multiplication factor here is represented by EQ3 below:

$$M(V')/M(V) = C \cdot \text{Exp}\{\alpha(V \pm \Delta V - V\text{th})\}/ \quad [EQ3]$$
$$C \cdot \text{Exp}\{\alpha(V - V\text{th})\}$$
$$= \text{Exp}(\pm \alpha \cdot \Delta V)$$

The CCD driver circuit 31 uses these relationship equations to calculate a sensitivity multiplication factor of the charge multiplying detector 64 from a voltage value of a sensitivity control pulse φCMD and outputs the sensitivity multiplication factor to the metering correcting circuit 37.

The analog processing circuit 33 has a preamplifier for multiplying CCD output signals from the CCD 19 and a CDS circuit for performing correlation dual sampling for reducing CCD noise. The signals CDS-processed in the analog processing circuit 33 are output to the A/D converter 34 and are converted to digital signals. The output of the A/D converter 34 is output to the digital processing circuit 35.

The digital processing circuit 35 performs signal processing such as cramp processing, white-balance processing, color conversion processing, electronic zoom processing, gamma conversion processing and image emphasis processing on video signals input from the A/D converter 34. Then, synchronization processing for three wavelengths is performed thereon and the result is output to the selector 40.

In the digital processing circuit 35, the white-balance processing defines different values for the normal light observation mode and the observation mode with multiple special light beams in accordance with a mode select signal from the mode select switch 58. The set values which are stored in the memory 22 corresponding to the observation modes are input to the digital processing circuit 35 through the CPU 30.

The selector 40 separates chronological images in the normal light mode or special light mode, which are output from the digital processing circuit 35, and outputs the resulting images to the triaxial simultaneous memories 41, 42 and 43.

The simultaneous memories 41, 42 and 43 store images in the normal light mode or special light mode and reads these three memories simultaneously to synchronize panel sequential images. Then, the simultaneous memories 41, 42 and 43 output the resulting images to the matrix circuit 44.

The matrix circuit 44 performs different kinds of color conversion processing in the normal light mode and in the special light mode in accordance with a mode select signal from the mode select switch 58.

In the special light mode, the matrix circuit 44 multiplies images from the simultaneous memories 41, 42 and 43 by a predetermined matrix coefficient for each selected special light mode and constructs a synthesized image. The matrix circuit 44 outputs the constructed image to the D/A converters 45, 46 and 47.

In the normal light mode, the matrix circuit 44 does not perform color conversion processing on images from the simultaneous memories 41, 42 and 43 but directly outputs the images to the D/A converters 45, 46 and 47.

The D/A converters 45, 46 and 47 convert and output the images from the matrix circuit 44 to analog video signals.

The 75-Ω driver 48 outputs analog video signals in the normal light mode and special light mode, which are input from the D/A converter 45, 46 and 47, to the monitor 6 and a peripheral device such as a storage device (not shown).

Figure 6:
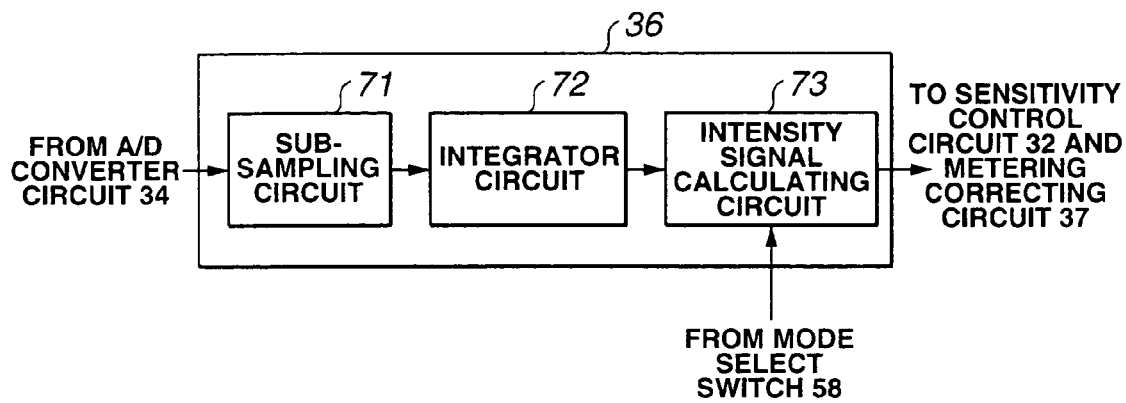

As shown in FIG. 6, the metering circuit 36 has a sub-sampling circuit 71, an integrator circuit 72, and an intensity signal calculating circuit 73.

The sub-sampling circuit 71 thins out and outputs to the integrator circuit 72 video signals corresponding to wavelengths of observation modes, which are input from the A/D converter 34. According to this embodiment, the sub-sampling by the sub-sampling circuit 71 can reduce the circuit size of the following integrator circuit 72.

The integrator circuit 72 integrates images in the normal light mode or special light mode, which are input from the sub-sampling circuit 71, for each field and calculates an integral for each field. The integrator circuit 72 outputs the integration result to the intensity signal calculating circuit 73.

The intensity signal calculating circuit 73 calculates an intensity signal based on the integral for each field of each wavelength, which is calculated by the integrator circuit 72.

The intensity signal calculation by the intensity signal calculating circuit 73 differs for each observation mode based on a mode select signal from the mode select switch 58.

In the normal light mode, the intensity signal calculating circuit 73 multiplies and adds the integrals of the R, G and B fields by 0.3, 0.59 and 0.11 and calculates the intensity signal.

In the special light mode, the intensity signal calculating circuit 73 multiplies the integrals of the fields by a predetermined coefficient and add the results to calculate the intensity signal.

The intensity signal calculated for each observation mode by the intensity signal calculating circuit 73 is output to the sensitivity control circuit 32 and the metering correcting circuit 37.

Figure 7:
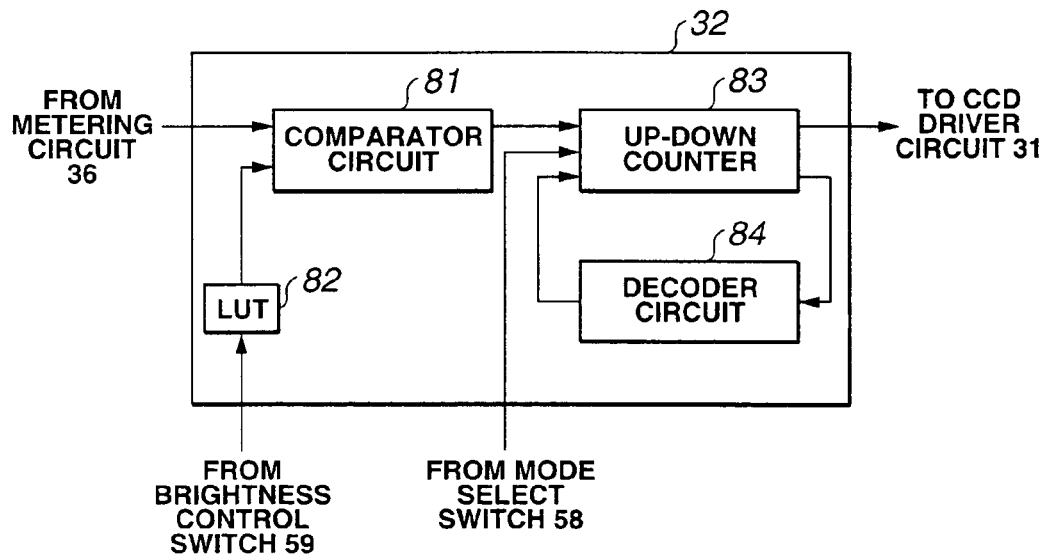

As shown in FIG. 7, the sensitivity control circuit 32 has a comparator circuit 81, a look-up table circuit (LUT circuit) 82, an up-down counter 83 and a decoder circuit 84.

The LUT circuit 82 converts and output to the comparing circuit 81 a level selected by an operator via the brightness control switch 59 to a target value.

In particular, the LUT circuit 82 includes multiple look-up tables (LUTs) corresponding to the normal light mode and the special light modes. The LUT circuit 82 selects an LUT in accordance with a mode select signal for the normal light mode or multiple special light modes selected via the mode select switch 58. Then, the LUT circuit 82 converts and outputs to the comparator circuit 81 a level selected via the brightness control switch 59 in the selected LUT to a target value.

The comparator circuit 81 compares the intensity signals of the normal light mode and special light modes input from the metering circuit 36 and the target value of the monitor brightness input from the LUT circuit 82 and outputs the comparison result to the up-down counter 83. The comparator circuit 81 further has a function for increasing the increment/decrements of the counter value in order to improve the responsivity of the sensitivity multiplication factor when a large difference exists between the intensity signal and the target value.

The up-down counter 83 counts up or down (C'=C±1) the counter value based on the result of the comparison between the intensity signal and the brightness target value, which is input from the comparator circuit 81. The up-down counter 83 outputs the counter value to the CCD driver circuit 31 and the decoder circuit 84.

The up-down counter 83 terminates the counter output when a stop signal is input from the decoder circuit 84 to the up-down counter 83. The up-down counter 83 terminates the counter output when a mode select signal from the mode select switch 58 is the normal light mode. That is, the sensitivity control circuit 32 operates only in the special light modes.

The decoder circuit 84 discriminates an overflow or an underflow based on the counter value input from the up-down counter 83 and outputs a stop signal to the up-down counter 83 when an overflow or underflow occurs.

In this case, as shown in FIG. 4, data of the sensitivity multiplication factor characteristic of the CCD 19, which is stored in the memory 22 of the storage device 20, may be a range from the threshold value Vth for starting charge multiplication to Vmax where the sensitivity multiplication factor is maximum, which is divided into the number equal to the total counter number of the up-down counter 83 and may be stored together with the voltage value (multiplicity) and the sensitivity multiplication factor. In a relationship between applied voltage and a sensitivity multiplication factor M(V), the stored data may be a parameter relating to a sensitivity multiplication factor such as C, α, Vth and Vmax based on $M(V)=C \cdot \text{Exp}\{\alpha(V-V_{th})\}$.

Figure 8:
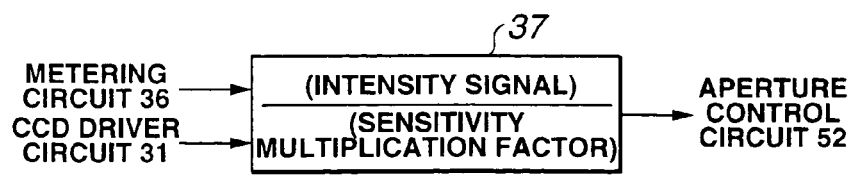

As shown in FIG. 8, the metering correcting circuit 37 performs a calculation for dividing an intensity signal by a sensitivity multiplication factor based on the intensity signals in the normal light mode and special light modes, which are input from the metering circuit 36 and the sensitivity multiplication factor of the charge multiplying detector 64, which is input from the CCD driver circuit 31. The metering correcting circuit 37 outputs the calculation result to the aperture control circuit 52.

The purpose of the metering correcting circuit 37 is to obtain an intensity signal corrected by an amount equal to the sensitivity multiplication factor of 1 by dividing the intensity signal by the sensitivity multiplication factor since the input intensity signal is calculated based on a CCD output value sensitivity-multiplied by the charge multiplying detector 64.

The mode select signal 58 is a switch used by an operator for selecting any observation mode from the normal light observation mode and the multiple special light observation (such as fluorescence observation, narrow band light observation, infrared light observation) modes.

The mode select switch 58 may be provided in the processor 3, a keyboard, a footswitch, the endoscope 2 or any other places.

The mode select signal (observation mode) selected by the mode select switch 58 is output to the rotating filter switching mechanism 56, the rotating filter control circuit 57, the metering circuit 36, the CCD driver circuit 31, the digital processing circuit 35, the matrix circuit 44 and the sensitivity control circuit 32.

The brightness control switch 59 is a switch used by an operator for selecting any one of brightness target values at multiple levels for the monitor screen.

The brightness control switch 59 is provided on a front panel of the processor 3.

A signal in response to an operation of the brightness control switch 59 is output to the sensitivity control circuit 32 and the aperture control circuit 52.

The light source apparatus 5 will be described in detail below.

The lamp 50 of the light source apparatus 5 includes a xenon lamp, a halogen lamp, an LED, and an LD (semiconductor laser) and so on and generates illumination light.

The condensing lens 55 gathers pencils of illumination light guided from the lamp 50 through the aperture 51 and the rotating filter 53 onto a back end surface of the light guide 12.

The aperture 51 and the rotating filter 53 are provided between the lamp 50 and the condensing lens 55. The rotating filter 53 is connected rotatably about a rotation axis of the motor 54 and is rotationally controlled at a predetermined speed by the rotating filter control circuit 57.

The rotating filter control circuit 57 can control a rotation speed of the rotating filter 53 (motor 54) to a predetermined rotation speed in accordance with a mode select signal from the mode select switch 58. The rotating filter control circuit 57 provides a different rotating speed to the rotating filter 53 in accordance with a selected observation mode. The rotating filter control circuit 57 defines the rotation speed in the special light observation mode to ½ of the rotation speed in the normal light mode.

An intensity signal is input from the metering correcting circuit 37 to the aperture control circuit 52. Then, the aperture control circuit 52 compares the intensity signal and a brightness target value selected by an operator via the brightness control switch 59. Based on the comparison result, the aperture control circuit 52 controls an amount of illumination light to the back end surface of the light guide 12 by controlling an opening/closing operation of the aperture 51 provided on the illumination light path between the lamp 50 and the rotating filter 53.

Figure 9:
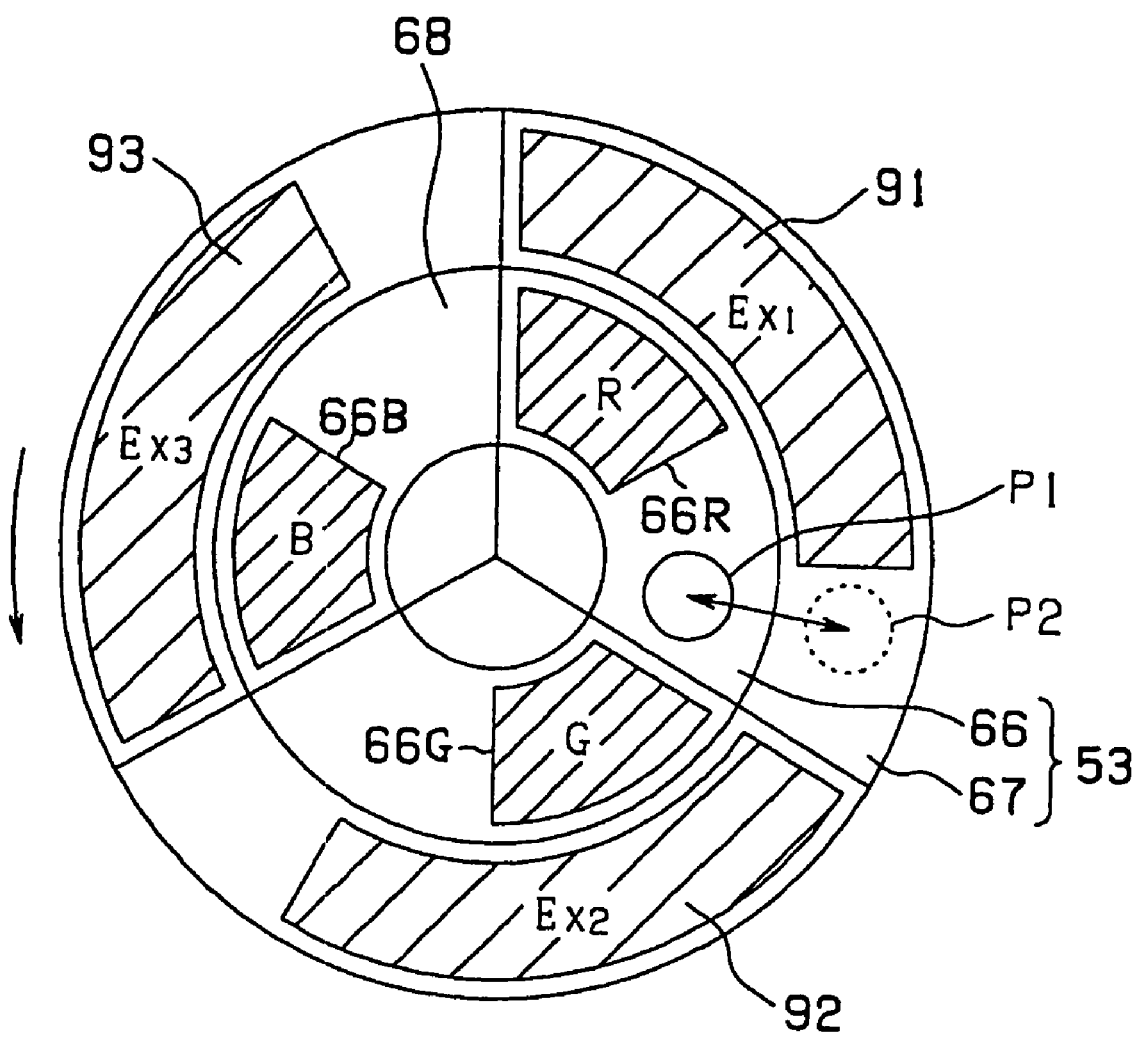

The rotating filter 53 has a dual structure having two filter sets 66 and 67 at the inner radius and at the outer radium as shown in FIG. 9.

The rotating filter switching mechanism 56 selectively moves one of the first filter set 66 at the inner radius and the second filter set 67 at the outer radius of the rotating filter 53 on the illumination light axis connecting the lamp 50 and the back end surface of the light guide 12 and moves the rotating filter 53 entirely. The rotating filter switching mechanism 56 may not move the rotating filter 53 in some special light observation modes.

In the normal light mode, the rotating filter switching mechanism 56 provides the filter set 66 at the inner radius onto the illumination light axis.

In the special light mode, the rotating filter switching mechanism 56 provides the filter set 67 at the outer radius onto the illumination light axis.

As shown in FIG. 9, the first filter set 66 at the inner radius of the rotating filter 53 has three filters 66R, 66G and 66B for R, G and B, respectively, for the normal light mode. The filters 66R, 66G and 66B have a spectral characteristic allowing light in red (R), green (G) and blue (B) wavelength bands to pass through.

The second filter set 67 at the outer radius has three Ex1, Ex2 and Ex3 filters 91, 92 and 93 each having a spectral characteristic for the special light mode (fluorescence observation).

For example, according to this embodiment, the Ex1 filter 91 is an exciting light filter allowing light in the 390 to 470 nm range to pass through.

The Ex2 filter 92 is a reflected light filter having a spectral characteristic having a narrow band with a center wavelength of about 550 nm and in the half breadth of about 30 nm and having the transmittance of several percent.

The Ex3 filter 93 is a reflected light filter having a spectral characteristic having a narrow band with a center wavelength of about 600 nm and in the half breadth of about 30 nm and having the transmittance of several percent.

Figure 12:
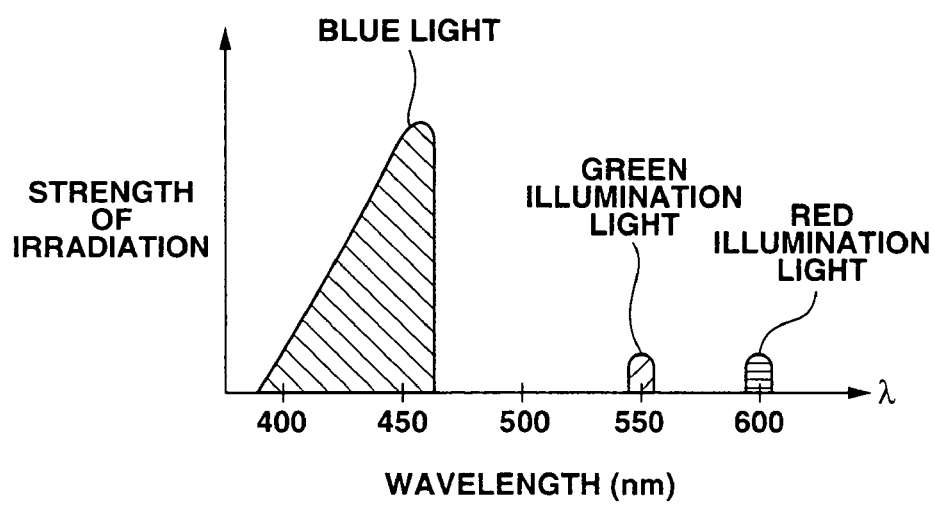

In the special light mode, the illumination light irradiated from the illumination lens 16 of the endoscope 2 has a spectral characteristic as shown in FIG. 12, for example.

The filters 66R, 66G and 66B correspond to light-exposure periods of the CCD 19. The light-shield areas 68 between the filters 66R, 66G and 66B correspond to light-shield periods (reading periods) of the CCD 19. The same is true for the second filter set 67.

The size of the second filter set 67 is defined about 1.5 times of the size of the first filter set 66 according to this embodiment. The rotational speed of the rotating filter 53 in the fluorescence observation mode is defined ½ of the rotational speed in the normal mode. The light-exposure time (accumulating time) in the special light mode is defined three times of the light-exposure time in the normal light mode. Since auto fluorescence is significantly weak, the light-exposure time is longer.

In FIG. 9, the filters 66R, 66G and 66B for normal light and the filters 91, 92 and 93 for special light are provided at the inner radius and at the outer radius, respectively, but may be provided oppositely.

A filter opening rate of the second filter set 67 may be the same as the one for normal light or may be different for each wavelength.

[Operation]

A way of using the endoscope apparatus 1 according to the first embodiment will be described below.

In order to start an endoscopic examination, an operator connects to the processor 3 the endoscope 2 of a type corresponding to a part to be observed and an observation type among multiple types of endoscope.

Thus, the CPU 30 of the processor 3 reads different kinds of data relating to the endoscope 2 stored in the memory 2 through the CPU 21 of the endoscope 2. Data of sensitivity multiplication factor characteristic (a relationship between a voltage value and a sensitivity multiplication factor) of the CCD 19 stored in the memory 22 is output to the CCD driver circuit 31 through the CPU 30.

Next, operations in the normal light mode and in a special light mode (for fluorescence observation) will be described.

An operator inserts the insert portion 11 of the endoscope 2 into the body cavity (the bronchi, the esophagus, the stomach, the colon, the neck, the abdominal cavity, the thorax, the bladder and the womb) and performs observation under normal light.

In order to perform observation under normal light (in the normal light mode), the rotating filter switching mechanism 56 has the first filter set 66 on the illumination light path. The sensitivity multiplication factor of the CCD 19 is defined 1 (without multiplication). Under this condition, illumination light irradiated from the lamp 50 passes through the first filter set 66 so that panel-sequential illumination light beams of R (red), G (green) and B (blue) are irradiated on the time series from the illumination lens 16 to a living-body tissue through the light guide 12 of the endoscope 2.

The metering circuit 36 calculates an intensity signal to be displayed on the monitor screen and outputs the intensity signal to the sensitivity control circuit 32 and the metering correcting circuit 37. In the normal light mode, the counter output from the sensitivity control circuit 32 to the CCD driver circuit 31 is terminated. Thus, the sensitivity control pulse ϕCMD is not output from the CCD driver circuit 31 to the CCD 19, but the sensitivity multiplication factor of the CCD 19 is one time.

Thus, data by the sensitivity multiplication factor of 1 (without multiplication) is output from the CCD driver circuit 31 to the metering correcting circuit 37. The metering correcting circuit 37 performs a division on an intensity signal from the metering circuit 36 and a sensitivity multiplication factor from the CCD driver circuit 31. Because of the sensitivity factor of 1, the same value as the output value from the metering circuit 36 is output to the aperture control circuit 52.

The aperture control circuit 52 compares the intensity signal and a brightness target value selected by an operator via the brightness control switch 59 and controls the opening/closing of the aperture 51 in accordance with the comparison result (brightness relationship). If the intensity signal is brighter than the target value, the aperture 51 is operated to close (that is, the irradiation strength to the back end surface of the light guide 12 is decreased). On the other hand, if the monitor screen is darker than the target value, the aperture 51 is operated to open (that is, the irradiation strength to the back end surface of the light guide 12 is increased). By changing the irradiation strength of the light to be irradiated to a living-body tissue, an automatic dimming operation is performed by controlling the aperture 51 (that is, automatic gain control through the opening/closing control of the aperture of the light source apparatus) such that the brightness of the monitor 6 can be maintained at a value set by an operator.

R, G and B light beams reflected by the living-body tissue sequentially enter the light receptive plane (that is, the image area 60) of the CCD 19. The signals output from the CCD 19, which correspond to the R, G and B reflected light beams, are input to the signal processor 4 and undergo different kinds of signal processing in the analog processing circuit 33 and the digital processing circuit 35. Then, the result is output to the monitor 6 and/or a peripheral apparatus such as a storage device through the selector 40, the simultaneous memories 41, 42 and 43, the matrix circuit 44 and the 75-Ω driver 48. Thus, normal light images can be displayed and/or recorded by the monitor 6 and/or the peripheral apparatus.

In the digital processing circuit 35, the R, G, and B white-balance coefficients are set values for the normal light mode, which are stored in the memory 22. In the matrix circuit 44, the R, G and B images are output without color converting processing.

Figure 11:
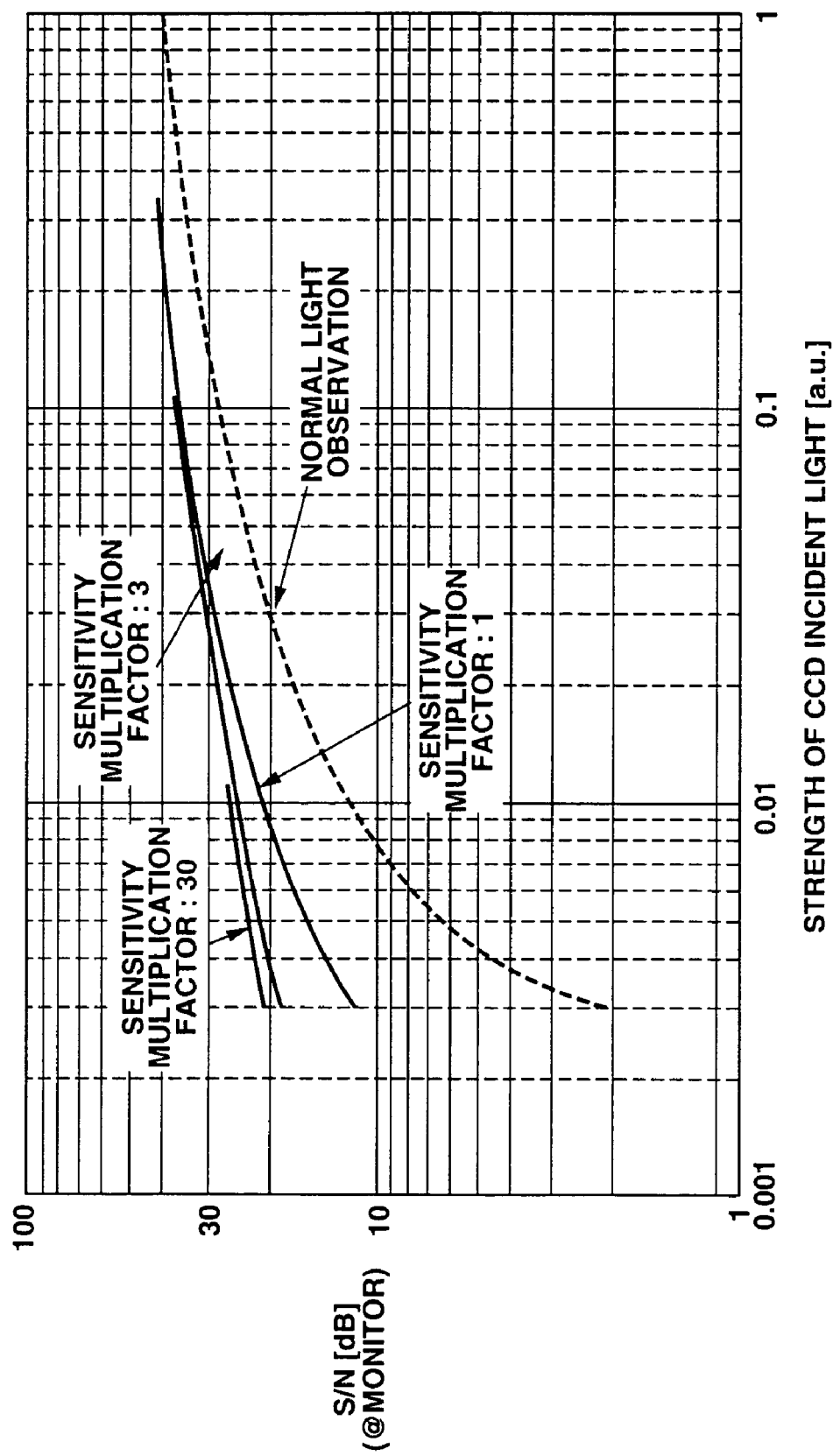

The output signals of the normal light images to be displayed on the monitor 6 and the S/N characteristic are indicated by dashed lines in FIGS. 1 and 11.

In order to perform a fluorescence observation (in the special light mode), an operator selects fluorescence observation mode from multiple observation modes via the mode select switch 58. In accordance with the selection instruction, the rotating filter switching mechanism 56 disposes the second filter set 67 of the rotating filter 53 on the illumination light path.

The illumination light irradiated from the lamp 50 of the light source apparatus 5 passes through the second filter set 67 of the rotating filter 53. Thus, blue light as exciting light of the filter Ex1, green illumination light of the filter Ex2 and red illumination light of the filter Ex3 are generated, which then enter the back end surface of the light guide 12 through the condensing lens 55. Then, the resulting light beams are irradiated on the time series as illumination light having a spectral characteristic (relating to the spectrum and the strength) as shown in FIG. 12, for example, from the illumination lens 16 at the distal end 15 of the endoscope 2 to the living-body tissue.

Figure 13:
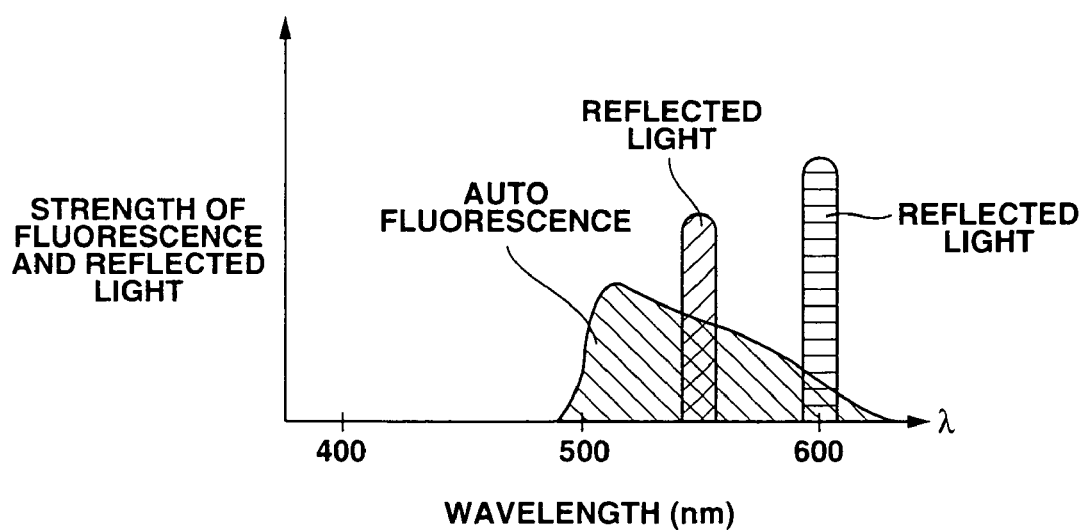

Irradiation of the exciting light to the living-body tissue causes reflected light (return light) of exciting light. Furthermore, weak auto fluorescence with a peak around 520 nm is emitted by the exciting light from the living-body tissue. The reflected light and the weak auto fluorescence enter the objective lens 17. However, the reflected light of the exciting light itself is cut by the exciting light cut filter 18, and only the auto fluorescence enters the light receptive surface of the CCD 19. The reflected light of green and red illumination light beams enters the objective lens 17, passes through the exciting light cut filter 18 and enters the light receptive surface of the CCD 19. Thus, light having spectral characteristics of auto fluorescence and reflected light as shown in FIG. 13 enter the light receptive surface of the CCD 19.

The fluorescence from the living-body tissue and the green and red reflected light beams sequentially enter the CCD 19. Then, the CCD output signals corresponding to the wavelengths are input to the signal processor 4 and undergo predetermined signal processing in the analog processing circuit 33 and the digital processing circuit 35. Then, fluorescent image is displayed and/or recorded by the monitor 6 and/or the storage device through the selector 40, the simultaneous memories 41, 42 and 43, the matrix circuit 44 and the 75-Ω driver 48. In order to image fluorescence and green and red reflected light, a white-balance coefficient from multiple coefficients stored in the memory 22 is defined for the fluorescence observation in the digital processing circuit 35. The matrix circuit 44 performs a predetermined color conversion on the output with different wavelengths, for example, such that the fluorescence, red reflected light and green reflected light can be output to a G-channel, a B-channel and an R-channel, respectively.

In order to observe a living-body tissue in the fluorescence observation mode, the strength of the light incident on the CCD 19 varies in accordance with a condition of the living-body tissue and a change in distance between the living-body tissue and the distal end 15 of the endoscope 2. As a result, the intensity signal of the monitor 6 may not agree with the target value (reference value) selected by an operator via the brightness control switch 59. In this case, dimming is performed as follows.

The metering circuit 36 calculates an intensity signal of a fluorescent image constructed from a wavelength of fluorescence and two wavelengths of reflected light and outputs the intensity signal to the sensitivity control circuit 32 and the metering correcting circuit 37. The comparator circuit 81 of the sensitivity control circuit 32 compares a brightness target value selected by an operator via the brightness control switch 59 and the intensity signal. Then, the up-down counter 83 outputs a counter value corresponding to the comparison result to the CCD driver circuit 31.

The CCD driver circuit 31 outputs a voltage value of the sensitivity control pulse φCMD to the charge multiplying detector 64 as a voltage corresponding to the counter value. The sensitivity multiplication factor of the CCD 19 increases or decreases in accordance with the voltage value of the sensitivity control pulse φCMD. The CCD driver circuit 31 changes the brightness of the image on the monitor 6 by increasing or decreasing the sensitivity multiplication factor so as to compensate an amount of change in strength of light entering the CCD 19 and controls such that the intensity signal can agree with the brightness target value.

The CCD driver circuit 31 calculates a sensitivity multiplication factor of the charge multiplying detector 64 from the voltage value of the sensitivity control pulse φCMD and outputs the calculated sensitivity multiplication factor to the metering correcting circuit 37. The metering correcting circuit 37 performs a calculation, [(intensity signal)/(sensitivity multiplication factor)] based on the intensity signal from the light measurement circuit 36 and the sensitivity multiplication factor from the CCD driver circuit 31 and outputs the intensity signal corrected by the sensitivity multiplication factor of 1 to the aperture control circuit 52. The aperture control circuit 52 compares the intensity signal and a brightness target value selected by an operator via the brightness control switch 59 and controls the opening/closing of the aperture 51 in accordance with the comparison result.

In this case, the endoscope apparatus 2 operates so as to close the aperture 51 if the intensity signal is brighter than the target value. The endoscope apparatus 2 operates so as to open the aperture 51 if the intensity signal is darker than the target value. Then, by changing the strength of the irradiation of illumination light to a living-body tissue, the endoscope apparatus 2 performs an automatic dimming operation through the control of the aperture 51 such that the brightness of the monitor 6 can agree with the target value.

Since the auto fluorescence is weak, the sensitivity multiplication factor of about 30 is required for achieving sufficient brightness on the monitor 6 when fluorescence on a living-body tissue is observed from a far point to a near point. Thus, the corrected intensity signal becomes significantly small, and the aperture 51 is controlled to open and is held at a full-open position. The sensitivity control circuit 32 compares the target value of the monitor brightness and the intensity signal. Then, by increasing or decreasing the voltage value (multiplicity) of the sensitivity control pulse φCMD from the CCD driver circuit 31 in accordance with the comparison result, the sensitivity multiplication factor is increased or decreased, and the intensity signal is changed.

Thus, the sensitivity control circuit 32 controls such that the intensity signal can agree with the brightness target value. In this case, an automatic dimming operation is performed only by using the sensitivity multiplication factor of the charge multiplying detector 64 of the CCD 19 (that is, a dimming operation under the control on a priority basis based on the sensitivity multiplication factor of the charge multiplying detector 64).

When a living-body tissue is fluorescence-observed at a near point and the strength of light entering the CCD 19 is increased to a normal light level, the sensitivity multiplication for the CCD 19 is not required. Thus, the sensitivity multiplication factor output from the CCD driver circuit 31 to the metering correcting circuit 37 is 1. Then, the metering correcting circuit 37 divides the intensity signal by the sensitivity multiplication factor. The metering correcting circuit 37 outputs the same value as the output value from the metering circuit 36 to the aperture control circuit 52 based on the sensitivity multiplication factor of 1. The aperture control circuit 52 compares the intensity signal and a brightness target value selected by an operator via the brightness control switch 59. Then, in accordance with the comparison result, the aperture control circuit 52 controls the opening/closing of the aperture 51. The aperture control circuit 52 operates so as to close the aperture 51 if the intensity signal is brighter than the target value. The aperture control circuit 52 operates so as to open the aperture 51 if the intensity signal is darker than the target value. In this case, an automatic dimming operation is performed only by using the aperture 51 (that is, a dimming operation under the control on a priority basis based on the aperture opening/closing operation).

When a living-body tissue is fluorescence-observed at a near point and the strength of light entering the CCD 19 is higher than that of the normal light, the condition with the sensitivity multiplication factor of 1 to 2 occurs, which increases the corrected intensity signal. Thus, in the aperture control circuit 52, the target value of the brightness selected by an operator via the brightness control switch 59 has the same level as the level of the corrected intensity signal. When the strength of the light entering the CCD 19 varies to be higher, the sensitivity multiplication factor gradually decreases. In connection with the gradual decrease in sensitivity multiplication factor, the aperture 51 operates gradually to the close state. When the strength of the light entering the CCD 19 varies to be lower, the aperture 51 operates gradually to the open state. In connection with the gradual movement to the open state, the sensitivity multiplication factor is controlled to gradually increase. In this case, in connection with the sensitivity multiplication factor of the charge multiplying detector 64 and the opening/closing of the aperture 51, an automatic dimming operation is performed at the same time (that is, a dimming operation based on the sensitivity multiplication factor and a dimming operation controlled in connection with the aperture opening/closing operation).

Figure 10:
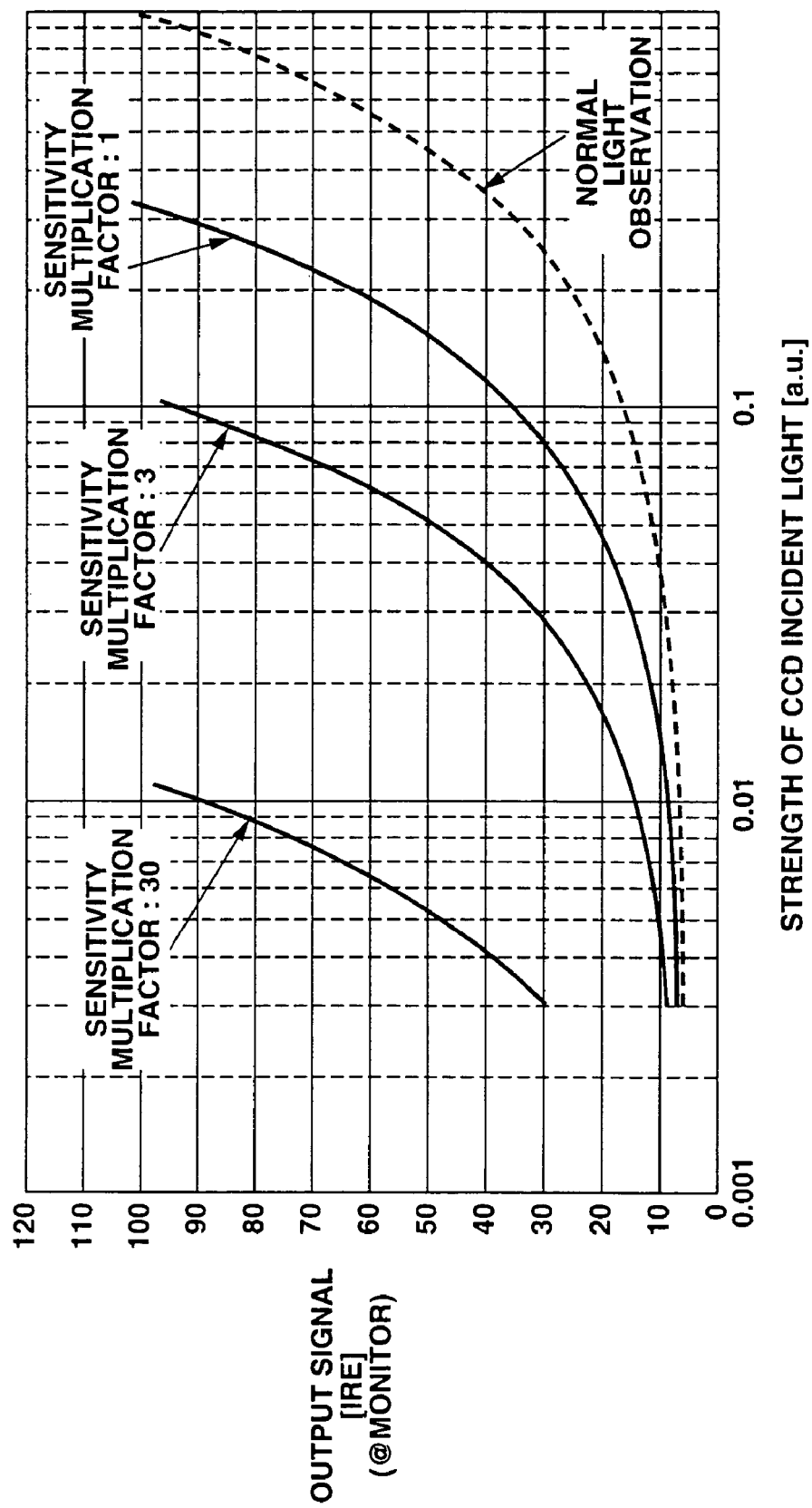

Thus, the output signals to be displayed on the monitor 6 and the S/N characteristic are indicated by solid lines in FIGS. 10 and 11. In the auto fluorescent area (in the vicinity of a part where the strength of CCD incident light is 0.01 [a.u.] in FIGS. 10 and 11), the more exposure time and higher sensitivity multiplication factor of the CCD 19 than those of the normal light mode can provide the output signals and S/N characteristic by the sensitivity multiplication factor of 1, 3, 30 and so on. In an auto fluorescent area, the characteristics (dashed-lines) during the normal light observation exhibit a darker monitor screen and a significantly poor S/N characteristic. However, by increasing the sensitivity multiplication factor of several tens of percent, the brightness of the monitor screen can be increased and a fluorescent image (that is, image synthesizing fluorescence and reflected light) with a high S/N characteristic (high image quality) is obtained. Here, any sensitivity multiplication factor can be multiplied by controlling the applied voltage value (multiplicity).

Fluorescence observation uses a characteristic that auto fluorescence having a peak in the vicinity of 520 nm is obtained when exciting light in the blue range is irradiated to a biological mucous membrane and the strength of the auto fluorescence is lower at a lesion part than that of a normal part. In fluorescence observation, by using green reflected light sharply capturing an influence of blood, that is, a hemoglobin absorbing band and red reflected light as reference light (that is a wavelength band without influences of the blood), a synthesized image obtained by imaging a part to be observed allows the removal of the influence of inflammation (of the blood) and the sharp observation of the presence of the lesion. For example, through fluorescence observation, blood vessels and inflammation are displayed in a color different from that of normal tissues while adenoma and cancer parts are displayed in a color different from those of normal tissues and inflammation and blood vessels. Thus, the fluorescence observation allows the easier pick-up detection of tumor lesion than that of the normal observation.

[Advantages]

According to the first embodiment, a dimming operation is performed properly in connection with the sensitivity multiplication factor of a sensitivity adjustable CCD and the aperture of a light source in the special light mode (fluorescence observation). Thus, the responsivity of the dimming operation can be improved, and a fluorescent image, which is an image synthesizing fluorescence and reflected light, can be obtained with more proper brightness and higher quality. Here, even when the strength of light entering the CCD 19 largely varies, the image saturation can be prevented.

Second Embodiment

Figure 14:
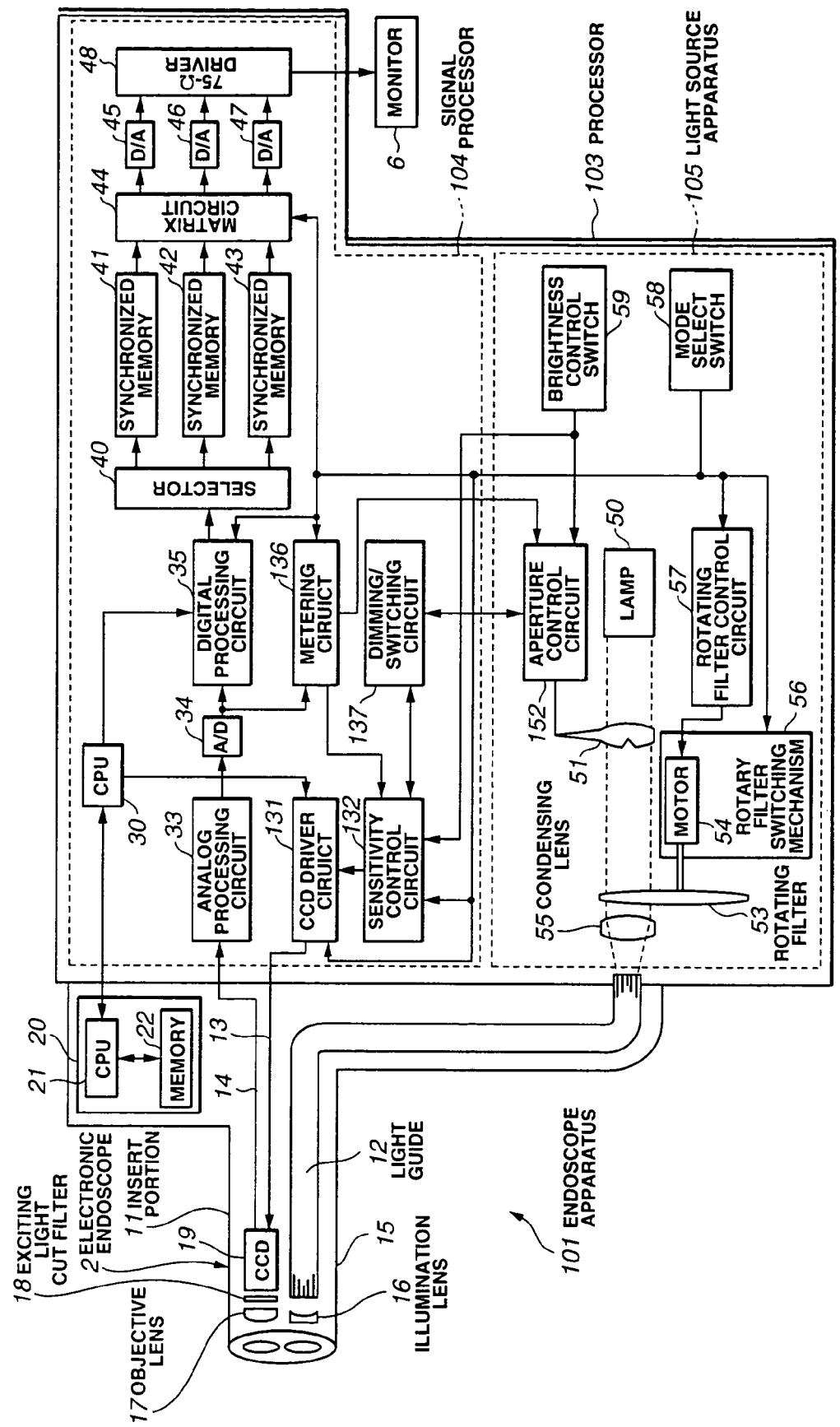
FIGS. 14 and 15 relate to a second embodiment of the present invention.
Figure 15:
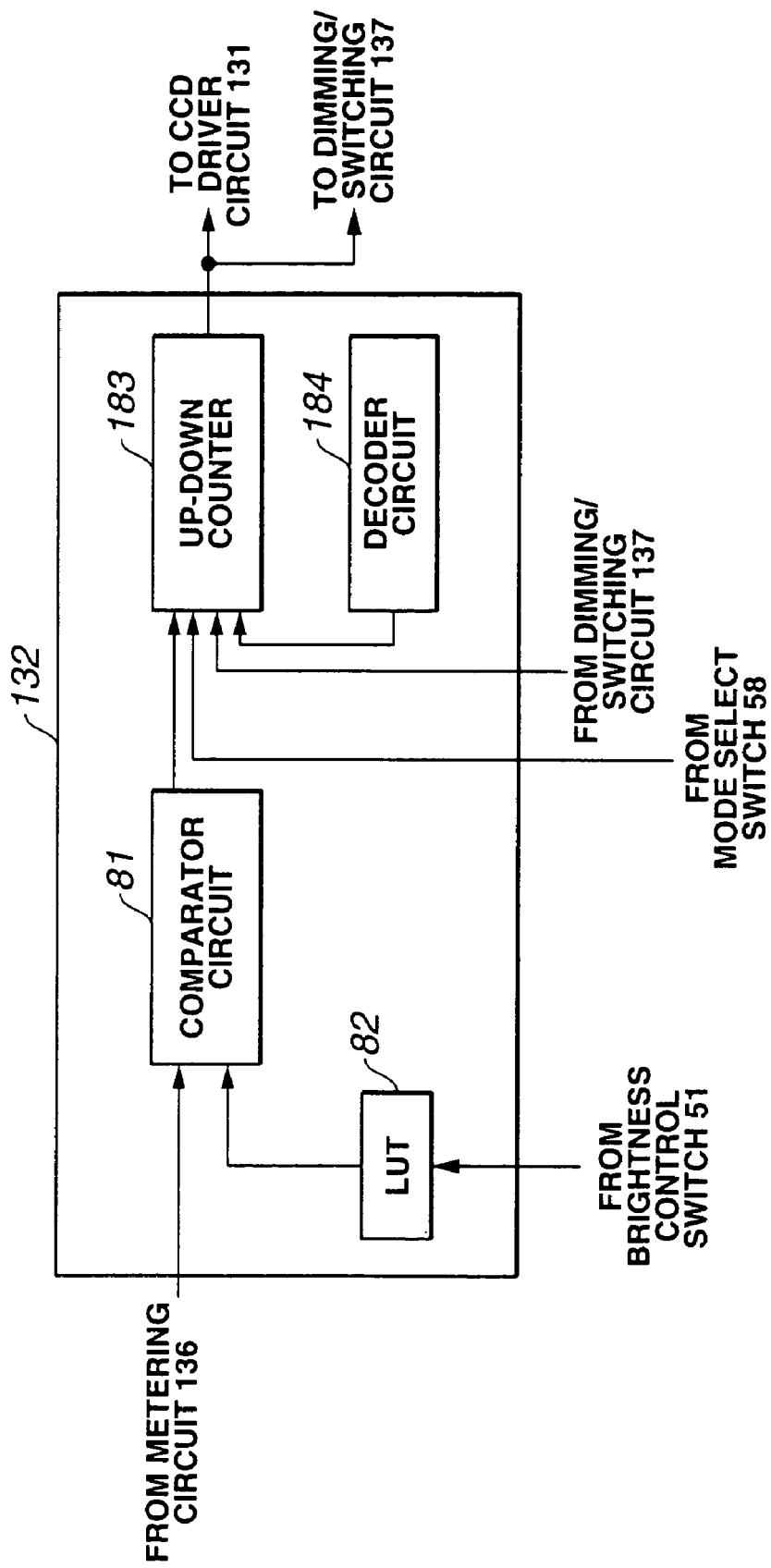

In the description of a second embodiment with reference to FIGS. 14 and 15, the same reference numerals are given to the same components as those of the first embodiment shown in FIGS. 1 to 13. Furthermore, the descriptions of the same components will be omitted here.

[Construction]

According to the first embodiment shown in FIGS. 1 to 13, the sensitivity multiplication factor of a sensitivity adjustable CCD and the aperture of a light source are connected during a dimming operation in a special light mode. On the other hand, according to the second embodiment shown in FIGS. 14 and 15, an endoscope apparatus 101 has a dimming/switching circuit 137. Here, a dimming operation is performed either by adjusting the sensitivity multiplication factor of the CCD 19 or by performing the aperture opening/closing operation.

As shown in FIG. 14, the endoscope apparatus 101 according to the second embodiment has an endoscope 2, a processor 103 and a monitor 6.

The endoscope 2 is removably connected to the processor 103. The processor 103 contains a signal processor 104 and a light source apparatus 105. The light source apparatus 105 may be provided separately from the processor 103.

The monitor 6 is connected to the processor 103 and displays video signals image-processed by the processor 103.

According to this embodiment, the signal processor 104 has a CPU 30, a CCD driver circuit 131, a sensitivity control circuit 132, an analog processing circuit 33, an A/D converter 34, a digital processing circuit 35, a metering circuit 136, a dimming/switching circuit 137, a selector 40, simultaneous memories 41, 42 and 43, a matrix circuit 44, D/A converters .45, 46 and 47 and a 75-Ω driver 48.

The light source apparatus 105 has a lamp 50, an aperture 51, an aperture control circuit 152, a rotating filter 53, a motor 54, a condensing lens 55, a rotating filter switching mechanism 56, a rotating filter control circuit 57, a mode select switch 58 and a brightness control switch 59.

Figure 5:
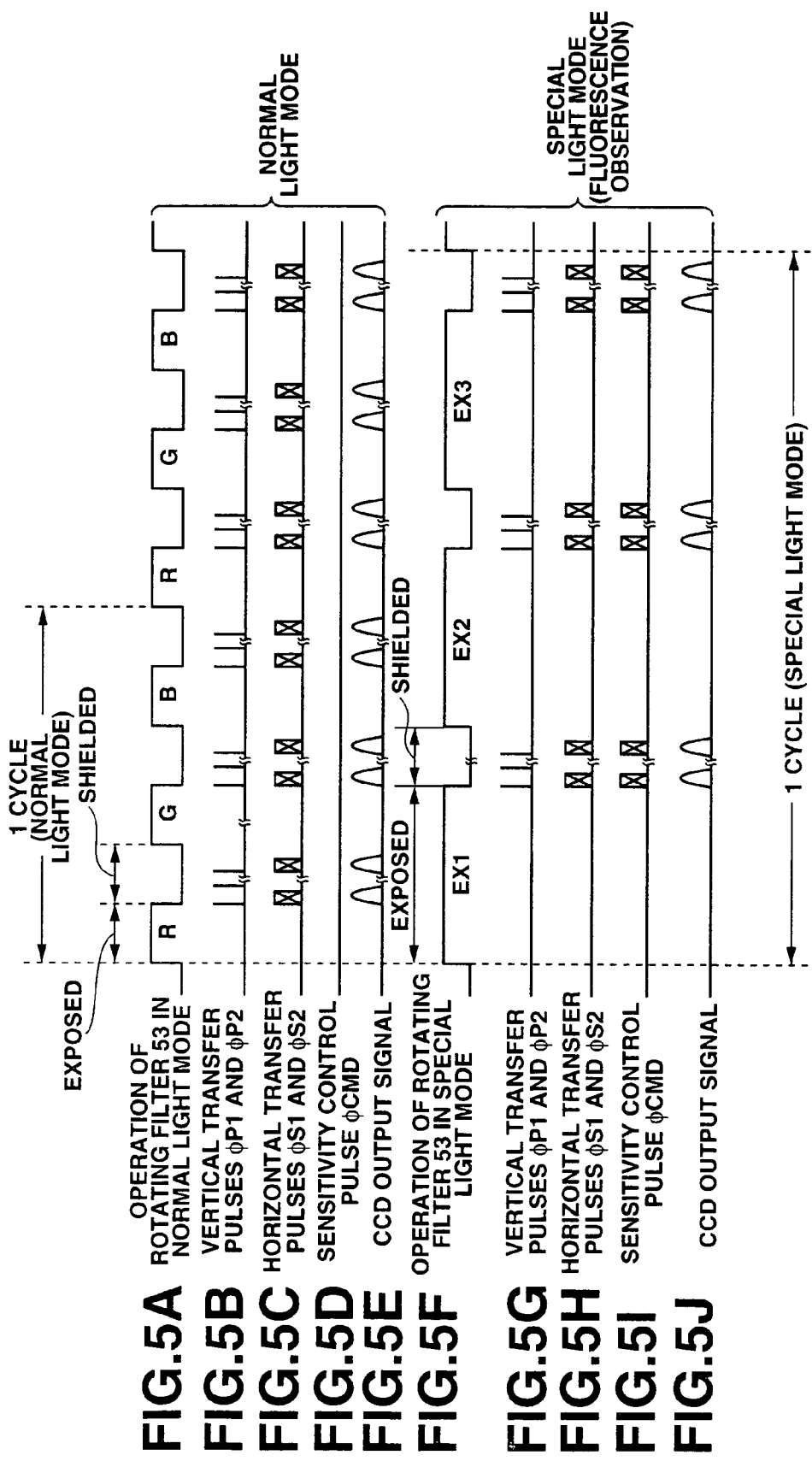

According to the second embodiment, operations (light-exposure and light-shield) of the rotating filter 53 in the normal light mode and in a special light (fluorescence observation) model timing of a drive signal supplied by the CCD driver circuit 131 to the CCD 19 and timing of a signal output from the CCD 19 are the same as those of the first embodiment shown in FIG. 5.

Counter values Cmin to Cmax are input from the sensitivity control circuit 132, which will be described later, to the CCD driver circuit 131.

The counter values Cmin to Cmax relate to a voltage value of the sensitivity control pulse φCMD output from the sensitivity control circuit 132 to the charge multiplying detector 64 (see FIG. 2) of the CCD 19.

Data of a sensitivity multiplication factor characteristic (that is, a relationship between applied voltage and the sensitivity multiplication factor) of the charge multiplying detector 64 (see FIG. 2) of the CCD 19 is input from the memory 22 of the storage device 20 to the CCD driver circuit 131 through the CPU 21 and the CPU 30.

The correspondence between the counter values Cmin to Cmax and voltage values Vth to Vmax (see FIG. 4) of voltage to be applied to the charge multiplying detector 64 (see FIG. 2) is defined such that the voltage Vth is provided when the counter value is the minimum Cmin while the voltage Vmax is provided when the counter value is the maximum Cmax.

The CCD driver circuit 131 outputs the sensitivity control pulse φCMD in the range from Vth to Vmax corresponding to the counter values Cmin to Cmax to the charge multiplying detector 64 (see FIG. 2) of the CCD 19.

Since the sensitivity multiplication factor characteristic of the CCD 19 varies due to variations in each CCD and/or drive signal lines, the CCD driver circuit 131 corrects the sensitivity multiplication factor characteristic such that the minimum value Vth and maximum value Vmax of the sensitivity control pulse φCMD voltage can correspond to the minimum Cmin and maximum Cmax of the counter values.

A relationship between a voltage value of the sensitivity control pulse φCMD to be supplied to the charge multiplying detector 64 (see FIG. 2) and the sensitivity multiplication factor of the CCD 19 is the same as that of the first embodiment.

Unlike the first embodiment, the metering circuit 136 outputs an intensity signal calculated for each observation mode to the sensitivity control circuit 132 and the aperture control circuit 152.

As shown in FIG. 15, the sensitivity control circuit 132 has a comparator circuit 81, an LUT circuit 82, an up-down counter 183 and a decoder circuit 184.

The up-down counter 183 counts up or down the counter value between Cmin and Cmax (where C'=C±1) based on a result from a comparison between an intensity signal input from the comparator circuit 81 and a brightness target value. The up-down counter 183 outputs the counter value to the CCD driver circuit 131, the dimming/switching circuit 137 and the decoder circuit 184. The up-down counter 183 stops the counter output at the maximum value Cmax when a stop signal is input from the decoder circuit 184. Furthermore, the up-down counter 183 sets the counter value at the minimum value Cmin when a mode select signal from the mode select switch 58 is the normal light mode. Thus, the counter operation is stopped. In other words, the sensitivity control circuit 132 operates only in special light modes.

The decoder circuit 184 judges whether or not the counter value input from the up-down counter 183 overflows or not. If so, the decoder circuit 184 outputs a stop signal to the up-down counter 183.

Here, the term, "overflow", refers to a state where the voltage value (multiplicity) of the sensitivity control pulse φCMD to be applied from the CCD driver circuit 131 to the charge multiplying detector 64 (see FIG. 2) is equal to the counter value Cmax corresponding to the maximum voltage Vmax.

The dimming/switching circuit 137 selects one of a dimming permit signal and a dimming stop signal and inputs the selected signal to the up-down counter 183. The up-down counter 183 starts a count operation in response to the input of the dimming permit signal and stops the count operation at the counter value Cmin in response to the input of the dimming stop signal.

In the light source apparatus 105, the aperture control circuit 152 is the only different component from that of the first embodiment.

An intensity signal is input from the metering circuit 136 to the aperture control circuit 152. The aperture control circuit 152 compares the intensity signal and a brightness target value selected by an operator via the brightness control switch 59. Subsequently, based on the comparison result, the aperture control circuit 152 controls the opening/closing of the aperture 51 provided on the optical path between the lamp 50 and the rotating filter 53 and controls an amount of illumination light to be irradiated to the back end surface of the light guide 12.

A dimming permit signal or a dimming stop signal is input from the dimming/switching circuit 137 to the aperture control circuit 152.

The aperture control circuit 152 starts controlling the opening/closing of the aperture 51 in response to the input of the dimming permit signal and fixes (or holds) the opening/closing position of the aperture 51 at a predetermined position in response to the input of the dimming stop signal. Here, the predetermined position refers to an opening/closing position of the aperture 51 allowing the maximum strength of the light entering to the back end surface of the light guide 12 and is at or near the full open (full aperture) state.

Thus, the endoscope apparatus 101 can be dimmed by two ways of adjusting the sensitivity multiplication factor of the CCD 19 and performing an opening/closing operation on the aperture 51 of the light source apparatus 105. The dimming/switching circuit 137 determines and selects one of the two dimming ways.

Counter values Cmin to Cmax showing the sensitivity multiplication factors are input from the sensitivity control circuit 132 to the dimming/switching circuit 137. When the counter value Cmin corresponding to the sensitivity multiplication factor of 1 is input to the dimming/switching circuit 137, the dimming/switching circuit 137 outputs a dimming stop signal to the sensitivity control circuit 132. The dimming/switching circuit 137 outputs a dimming permit signal to the aperture control circuit 152 in synchronization with the output of a dimming stop signal to the sensitivity control circuit 132.

Opening/closing position information of the aperture 51 is input from the aperture control circuit 152 to the dimming/switching circuit 137. When the aperture 51 reaches a predetermined position, the dimming/switching circuit 137 outputs a dimming stop signal to the aperture control circuit 152. The dimming/switching circuit 137 outputs a dimming permit signal to the sensitivity control circuit 132 in synchronization with the output of a dimming stop signal to the aperture control circuit 152.

The dimming/switching circuit 137 does not output a dimming permit signal or a dimming stop signal to both of the sensitivity control circuit 132 and the aperture control circuit 152 but outputs a dimming permit signal to one of the circuits and a dimming stop signal to the other circuit.

[Operation]

Dimming during a fluorescence observation according to the second embodiment will be described.

In order to observe a living-body tissue by fluorescence observation, the strength of light entering the CCD 19 varies with the change in state of the living-body tissue and in distance between the living-body tissue and the distal end 15 of the endoscope 2. Thus, the brightness screen average value of the monitor 6 may no longer agree with a target value selected by an operator via the brightness control switch 59.

In this case, the metering circuit 136 calculates an intensity signal of a fluorescent image including a fluorescent wavelength and two wavelengths of reflected light and outputs the intensity signal to the sensitivity control circuit 132 and the aperture control circuit 152.

When a fluorescence observation is performed on a living-body tissue with far-point to near-point distances and when the strength of light entering the CCD 19 is much smaller than that of the normal light observation, a dimming operation is performed as follows.

In this case, the dimming/switching circuit 137 outputs a dimming permit signal to the sensitivity control circuit 132 and outputs a dimming stop signal to the aperture control circuit 152.

The sensitivity control circuit 132 causes the comparator circuit 81 to compare a brightness target value selected by an operator via the control switch 59 and the intensity signal. Then, the counter value from Cmin to Cmax counted up or down in accordance with the comparison result is output from the up-down counter 183 to the CCD driver circuit 131 and the dimming/switching circuit 137.

The CCD driver circuit 131 outputs a voltage from Vth to Vmax corresponding to the counted up or down counter value from Cmin to Cmax as the sensitivity control pulse φCMD to be applied to the charge multiplying detector 64 (see FIG. 2). In accordance with the increase/decrease in voltage of the sensitivity control pulse φCMD, the sensitivity multiplication factor of the CCD 19 increases or decreases. The sensitivity control circuit 132 changes the intensity signal to compensate an amount of change in strength of light entering the CCD 19 and performs automatic gain control such that the intensity signal can agree with the brightness target value.

Since a dimming stop signal is input from the dimming/switching circuit 137 to the aperture control circuit 152, the aperture control circuit 152 forcefully stops an opening/closing operation of the aperture 51. The aperture 51 is fixed (held) at a predetermined position. Thus, the strength of irradiation to the back end surface of the light guide 12 becomes maximum.

When a fluorescence observation is performed on a living-body tissue at a near-point distance and when the strength of light entering the CCD 19 is equal to that of the normal light observation, a dimming operation is performed as follows.

In this case, the dimming/switching circuit 137 outputs a dimming permit signal to the aperture control circuit 152 and outputs a dimming stop signal to the sensitivity control circuit 132.

The aperture control circuit 152 compares the intensity signal and a brightness target value selected by an operator via the brightness control switch 59 and controls the opening/closing operation of the aperture 51 in accordance with the comparison result.

If the intensity signal is brighter than the target value, the aperture control circuit 152 causes the aperture 51 to operate to close. If the monitor screen is darker than the target value, the aperture control circuit 152 causes the aperture 51 to operate to close. Thus, the aperture control circuit 152 controls such that the strength of irradiation of illumination light to the living-body tissue can be changed and the brightness of the monitor screen can be maintained at the target value selected by the operator.

On the other hand, since a dimming stop signal is input from the dimming/switching circuit 137 to the sensitivity control circuit 132, the up-down counter 183 is forcefully stopped. The counter value Cmin is output to the CCD driver circuit 131 and the dimming/switching circuit 137. The sensitivity multiplication factor of the CCD 19 is fixed at 1.

When a fluorescence observation is performed on a living-body tissue substantially at a near-point distance and when the strength of light entering the CCD 19 is smaller than that of the normal light observation, a dimming operation is performed as follows.

In this case, the dimming/switching circuit 137 alternately outputs dimming permit signals or dimming stop signals to the aperture control circuit 152 and the sensitivity control circuit 132 in accordance with the state.

When the strength of incident light to the CCD 19 is changed to decrease by the sensitivity multiplication factor of 1 to 2, the voltage value of the sensitivity control pulse φCMD from the CCD driver circuit 131 gradually decreases. In accordance with the gradual decrease in voltage value, the sensitivity multiplication factor of the CCD 19 also decreases, and the sensitivity multiplication factor becomes 1.

The counter value output from the up-down counter 183 to the dimming/switching circuit 137 is the minimum counter value Cmin corresponding to the sensitivity multiplication factor of 1. Therefore, the dimming/switching circuit 137 outputs a dimming stop signal to the sensitivity control circuit 132 and stops the operation of the up-down counter 183.

Thus, the counter value output to the CCD driver circuit 131 is fixed at the minimum counter value Cmin, and the sensitivity multiplication factor of the CCD 19 is fixed at 1.

On the other hand, the dimming/switching circuit 137 outputs a dimming permit signal to the aperture control circuit 152 and permits the opening/closing operation of the aperture 51. Then, the aperture control circuit 152 compares the intensity signal and a brightness target value selected by an operator via the brightness control switch 59 and controls the opening/closing operation of the aperture 51 in accordance with the comparison result.

When the strength of incident light to the CCD 19 is changed to increase while the aperture 51 is operating, the aperture 51 operates to open and reaches a predetermined position. The aperture positional information output from the aperture control circuit 152 to the dimming/switching circuit 137 is the predetermined position. Then, the dimming/switching circuit 137 outputs a dimming stop signal to the aperture control circuit 152, and the opening/closing position of the aperture 51 is fixed at the predetermined position.

On the other hand, the dimming/switching circuit 137 outputs a dimming permit signal to the sensitivity control circuit 132 and permits a counter operation of the up-down counter 183. Then, the sensitivity control circuit 132 compares the intensity signal and a brightness target value selected by an operator via the brightness control switch 59. In accordance with the comparison result and by counting up or down the counter value, the voltage value of the sensitivity control pulse φCMD to be output by the CCD driver circuit 131 is increased or decreased. Thus, the sensitivity control circuit 132 controls the sensitivity multiplication factor of the CCD 19 to increase or decrease.

[Advantages]

According to the second embodiment, a dimming operation is performed on the sensitivity multiplication factor of a sensitivity adjustable CCD and the aperture of a light source separately in a proper manner in a special light mode (fluorescence observation). Thus, even when the strength of the incident light to the CCD varies largely, the saturation of a fluorescent image, which is an image synthesizing fluorescence and reflected light, can be prevented. Therefore, the fluorescent image can have proper brightness and high quality.

Third Embodiment

In the description of a third embodiment with reference to FIGS. 16 to 21, the same reference numerals are given to the same components as those of the first embodiment shown in FIGS. 1 to 13. Furthermore, the descriptions of the same components will be omitted here.

[Construction]

Figure 16:
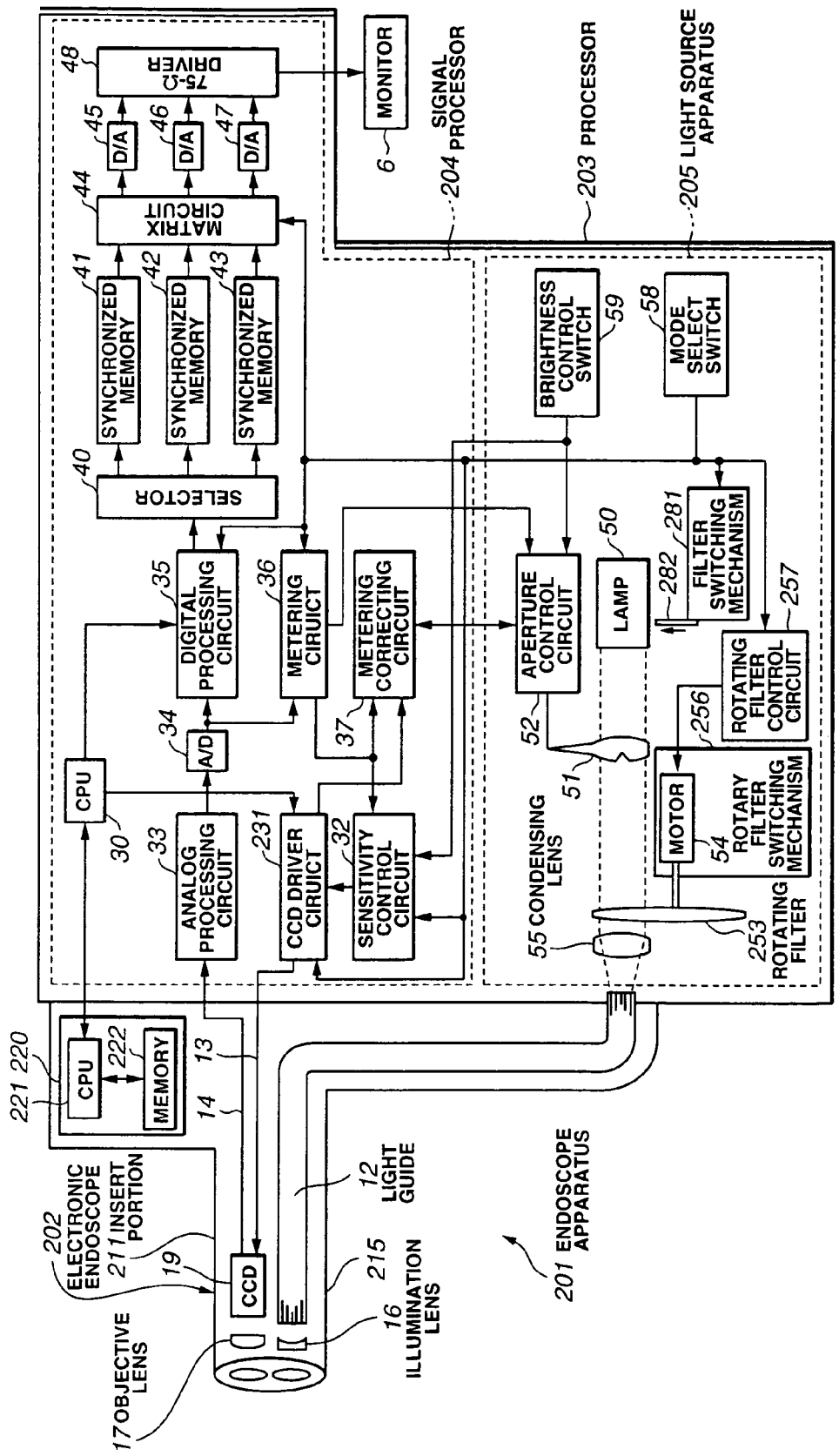
FIGS. 16 to 21 relate to a third embodiment of the present invention.

As shown in FIG. 16, an endoscope apparatus 201 according to a third embodiment is available for narrow-band light observation in a special light mode. The endoscope apparatus 201 has an endoscope 202, a processor 203 and a monitor 6.

The endoscope 202 is removably connected to the processor 203. The processor 203 contains a signal processor 204 and a light source apparatus 205. The light source apparatus 205 may be provided separately from the processor 203.

The endoscope 202 has a long and narrow insert portion 211 to be inserted to the body cavity of a patient.

The insert portion 211 contains a light guide 12, a CCD drive signal line 13 and a CCD output signal 14.

The distal end side of the light guide 12, an illumination lens 16, an objective lens 17 and a CCD 19 are provided at a distal end 215 of the insert portion 211. However, according to the third embodiment, an exciting light cut filter is not provided at the distal end 215.

The light guide 12 guides illumination light from the light source apparatus 205 in the processor 203 to the distal end 215 of the insert portion 211.

Light from an object is imaged on a light receptive surface of the CCD 19 through the objective lens 17.

The CCD 19 is connected to the CCD driver means 231 of the signal processor 204 within the processor 203 through the drive signal line 13. The CCD 19 controls an electronic shutter and accumulates signal charges in response to a drive signal generated by the CCD driver circuit 231.

The object image formed on the light receptive surface of the CCD 19 through the objective lens 17 is optoelectronically converted at pixels of the CCD 19 and is output from the floating diffusion amplifier.

The signals output from the CCD 19 are output to the analog processing circuit 33 of the signal processor 204 in the processor 203 through the CCD output signal line 14.

The endoscope 202 includes a storage device 220. The storage device 220 includes a CPU 221 and a nonvolatile memory 222.

The CPU 221 controls data-reading/-writing from/to the memory 222 and controls exchanges (communications) of data with the processor 203.

The memory 222, as storage means, stores accumulating time (speed of electronic shutter) of three wavelengths of R, G and B in the normal light mode and accumulation time (speed of electronic shutter) of the three wavelengths in special light modes (narrow-band light observation).

According to this embodiment, the signal processor 204 has a CPU 30, a CCD driver circuit 231, a sensitivity control circuit 32, an analog processing circuit 33, an A/D converter 34, a digital processing circuit 35, a metering circuit 36, a metering correcting circuit 37, a selector 40, simultaneous memories 41, 42 and 43, a matrix circuit 44, D/A converters 45, 46 and 47, and a 75-Ω driver 48.

The light source apparatus 205 has a lamp 50, an aperture 51, an aperture control circuit 52, a rotating filter 253, a motor 54, a condensing lens 55, a rotating filter switching mechanism 256, a rotating filter control circuit 257, a mode select switch 58, a brightness control switch 59, a filter switching mechanism 281 and an option filter 282.

FIGS. 17A to 17E are timing charts of drive signals and output signals of the CCD 19 for one wavelength of three wavelengths. FIG. 17A shows an operation of the rotating filter 253. FIG. 17B shows vertical transfer pulses φP1 and φP2. FIG. 17C shows a sensitivity control pulse φCMD in a special light mode. FIG. 17D shows horizontal transfer pulses φS1 and φS2. FIG. 17E shows output signals from the CCD 19.

Figure 17:
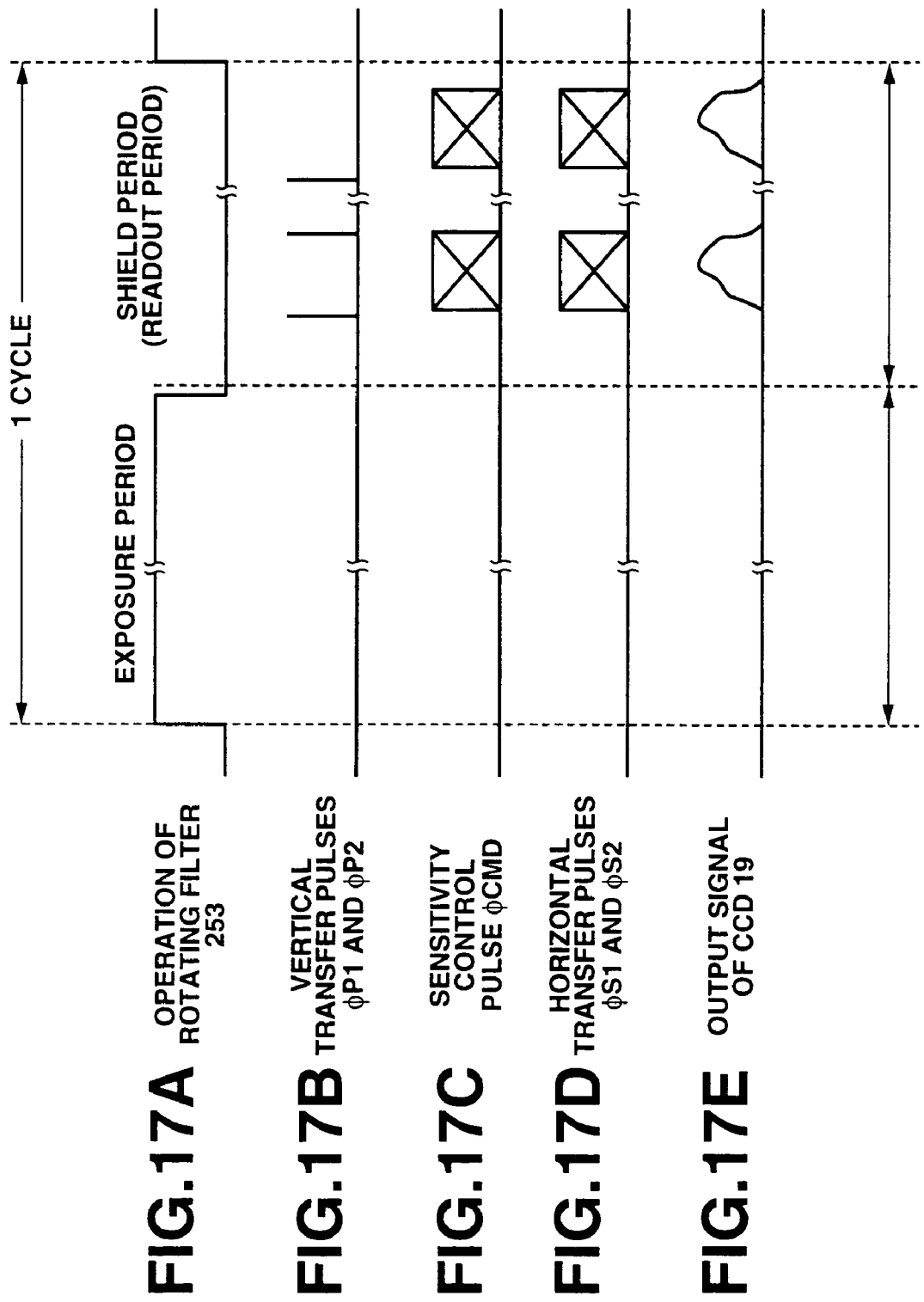

The CCD 19 can optoelectronically convert and integrate light entering from an object to the light receptive surface of the CCD 19 as signal charges in the exposure period showing FIG. 17.

In the shield period shown in FIG. 17A, the CCD driver means 131 outputs to the CCD 19 the vertical transfer pulses φP1 and φP2 shown in FIG. 17B, the horizontal transfer pulses φS1 and φS2 shown in FIG. 17D and a sensitivity control pulse φCMD (in a special light mode) shown in FIG. 17C.

The CCD 19 transfers signal charges integrated during the exposure period to a horizontal transfer register through the vertical transfer pulses φP1 and φP2 shown in FIG. 17B for each horizontal line. Then, the CCD 19 sequentially transfers the signal charges to the floating diffusion amplifier of the CCD 19 through the horizontal transfer pulses φS1 and φS2 shown in FIG. 17D. The floating diffusion amplifier converts the signal charges to voltage and outputs the result as output signals shown in FIG. 17E.

Here, according to this embodiment, the rotating filter 253 has a transmitting portion and a shielding portion in order to provide equal exposure periods (integrating time) to both normal light mode and special light (narrow-band light observation) mode.

The timing of drive signals excluding the sensitivity control pulse φCMD from the CCD 19 and the timing of the output from the CCD 19 are the same in the normal light mode and in the special light (narrow-band light observation) mode.

The rotating filter 253 is provided on the illumination light path between the lamp 50 and the condensing lens 55 and is connected to an axis of rotation of the motor 54. The rotating filter 253 rotates at a predetermined speed under the control of the rotating filter control circuit 257.

The rotating filter control circuit 257 can arbitrarily control the rotation speed of the rotating filter 253 (and the motor 54).

According to this embodiment, the rotation speed in the special light mode (for narrow-band light observation) under the control of the rotating filter control circuit 257 is equal to the rotation speed in the normal light mode.

The rotating filter switching mechanism 256 selectively moves a first filter set at the inner radius of the rotating filter 253 and a second filter set at the outer radius of the rotating filter 253 on the axis of illumination light connecting the lamp 50 and the back end surface of the light guide 12. Thus, the rotating filter switching mechanism 256 can move the entire rotating filter 253. The rotating filter switching mechanism 256 may not move the rotating filter 253 for some kinds of special light observation. The rotating filter switching mechanism 256 does not move the rotating filter 253 for narrow-band light observation like the normal light observation.

The option filter 282 has a transmittance characteristic limiting at least one wavelength band in comparison with the rotating filter 253 for R, G and B broad band wavelengths.

According to this embodiment, the option filter 282 has a transmittance characteristic with a three-peak pattern as described below.

The B' transmittance characteristic of the option filter 282 has the center wavelength of 415 nm and the half-value breadth of 30 nm. The G' transmittance characteristic of the option filter 282 has the center wavelength of 540 nm and the half-value breadth of 30 nm. The R' transmittance characteristic of the option filter 282 has the center wavelength of 620 nm and the half-value breadth of 30 nm.

Figure 18:
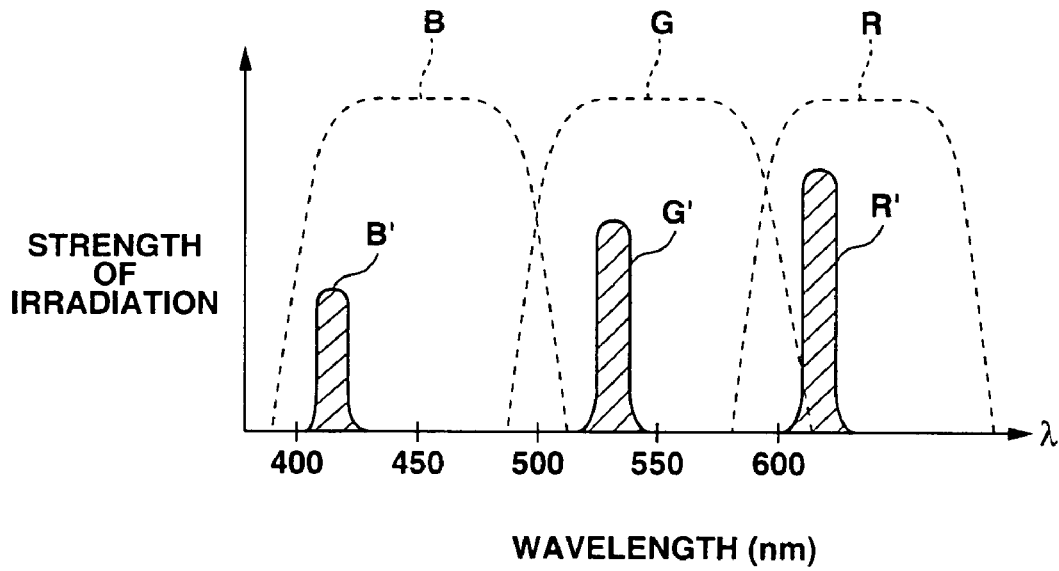

When the option filter 282 is provided on an illumination light axis connecting the lamp 50 and the back end surface of the light guide 12, illumination light irradiated from the lamp 50 passes through the option filter 282 and the rotating filter 253. Then, illumination light with a narrow-band spectral characteristic as indicated by solid lines in FIG. 18 enters the back end surface of the light guide 12. The dashed lines in FIG. 18 show a broad band spectral characteristic of R, G and B by the rotating filter 253.

The filter switching mechanism 281 can move the option filter 282 entirely. The filter switching mechanism 281 moves (provides and removes) the option filter 282 on the illumination light axis connecting the lamp 50 and the back end surface of the light guide 12.

The filter switching mechanism 281 operates in accordance with a mode select signal (narrow-band light) from the mode select switch 58.

The filter switching mechanism 281 removes the option filter 282 from the illumination light path in the normal light mode and provides the option filter 282 on the illumination light path in a special light mode (narrow-band light observation).

[Operation]

A way of using the endoscope apparatus 201 according to the third embodiment will be described below.

In order to start an endoscopic examination, an operator connects the endoscope 202 of a type corresponding to a part to be observed or a type of observation among multiple kinds of endoscopes to the processor 203. The CPU 30 of the processor 203 reads different kinds of data relating to the endoscope 202, which are stored in the memory 222, through the CPU 221 of the storage device 220 of the endoscope 202. Data of a sensitivity multiplication factor characteristic (a relationship between a voltage value and a sensitivity multiplication factor) of the CCD 19, which is stored in the memory 222, is output to the CCD driver circuit 231 through the CPU 30.

Next, an operation in a narrow-band light observation used as a special light mode will be described.

In order to perform a narrow-band light observation, an operator selects the narrow-band light observation from multiple observation modes of the mode select switch 58. In synchronization with the selection, the filter switching mechanism 281 operates, and the option filter 282 is provided on an illumination light path from the lamp 50 to the light guide 12. The rotating filter switching mechanism 256 does not operate while the rotating filter 253 has the same first filter set on the illumination light path as that of the normal light observation.

Illumination light irradiated from the lamp 50 of the light source apparatus 205 passes through the option filter 282 and the first filter set of the rotating filter 253. Narrow-band illumination light in R', G' and B' wavelength regions as shown in FIG. 18 enters the back end surface of the light guide 12 through the condensing lens 55 and is irradiated from the illumination lens 16 at the distal end 215 of the endoscope 202 to a living-body tissue on a time-series basis.

The narrow-band reflected light (return light) having been irradiated to the living-body tissue enters the light receptive surface of the CCD 19 through the objective lens 17. In this case, light having a spectral characteristic as shown in FIG. 19 enters the light receptive surface of the CCD 19.

Figure 19:
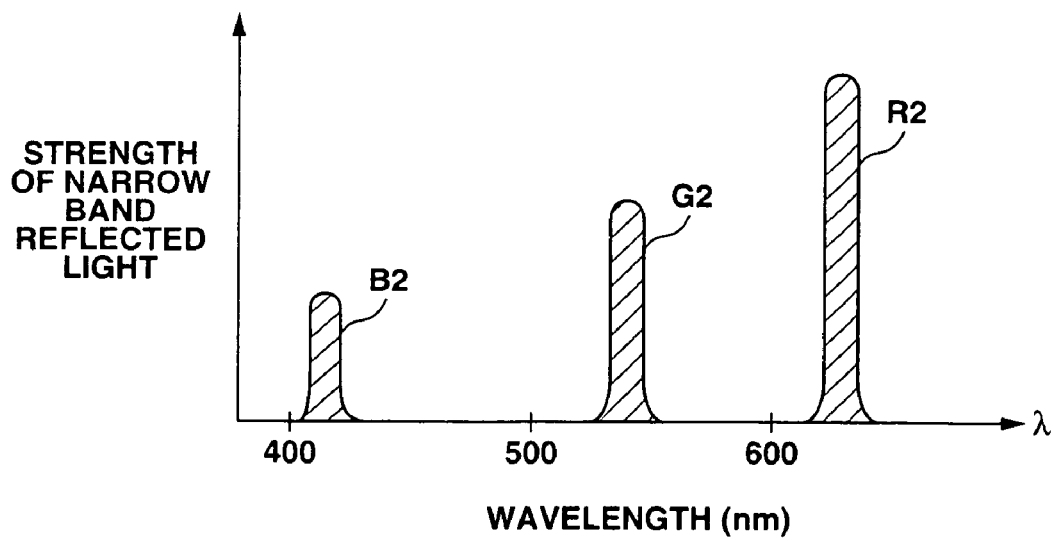

The narrow-band reflected light of blue (B2), green (G2) and red (R2) from the living-body tissue shown in FIG. 19 sequentially enters the CCD 19, and output signals of the CCD 19 corresponding to the wavelengths are input to the signal processor 204. Then, the signals undergo predetermined signal processing in the analog processing circuit 33, and the digital processing circuit 35 and are output to the monitor 6 and a peripheral apparatus through the selector 40, the simultaneous memories 41, 42 and 43, the matrix circuit 44 and the 75-Ω driver 48. Thus, an image of the narrow-band reflected light is displayed and is recorded.

For narrow-band light observation from multiple coefficients stored in the memory 222, the digital processing circuit 35 defines a white-balance coefficient to be used for imaging narrow-band reflected light of blue, green and red. The matrix circuit 44 performs a predetermined color conversion on images with the wavelengths.

In order to observe a living-body tissue by the narrow-band light observation, the strength of incident light to the CCD 19 varies in connection with changes in state of the living-body tissue and distance between the living-body tissue and the distal end 215 of the endoscope 202. Then, the intensity signal of the monitor 6 may not agree with the target value selected by an operator via the brightness control switch 59. In this case, a dimming is performed as follows.

The metering circuit 36 calculates an intensity signal of the narrow-band light image including the narrow-band reflected light with three wavelengths and outputs the intensity signal to the sensitivity control circuit 32 and the metering correcting circuit 37. The sensitivity control circuit 32 compares a brightness target value selected by an operator via the brightness control switch 59 in a comparator circuit.(refer to the comparator circuit 81 in FIG. 7) with the intensity signal. In accordance with the comparison result, the sensitivity control circuit 32 outputs a counter value counted up or down by a up-down counter (refer to the up-down counter 83 in FIG. 7) to the CCD driver circuit 231. The CCD driver circuit 231 leads the sensitivity control pulse φCMD to be output to the charge multiplying detector 64 (see FIG. 2) of the CCD 19 to the voltage value corresponding to the counted-up or-down counter value. Thus, the sensitivity multiplication factor of the CCD 19 increases or decreases in accordance with the voltage value of the sensitivity control pulse φCMD. In the entire endoscope apparatus 201, the sensitivity multiplication factor of the CCD 19 is increased or decreased so as to compensate an amount of change in strength of incident light to the CCD 19, and the brightness of the monitor 6 is changed. Therefore, the intensity is controlled to agree with the brightness target value.

The CCD driver circuit 231 outputs the sensitivity multiplication factor of the charge multiplying detector 64 (see FIG. 2) to the metering correcting circuit 37. The metering correcting circuit 37 performs a calculation of [(intensity signal)/(sensitivity multiplication factor)] based on the intensity signal from the metering circuit 36 and the sensitivity multiplication factor from the CCD driver circuit 231. Thus, the intensity signal by the sensitivity multiplication factor of 1 is output to the aperture control circuit 52.

The aperture control circuit 52 compares the intensity signal with a brightness target value selected by an operator via the brightness control switch 59 and controls the opening/closing of the aperture 51 in accordance with the comparison result.

If the intensity signal is brighter than the target value, the aperture control circuit 52 operates the aperture 51 to close. On the other hand, if the intensity signal is darker than the target value, the aperture control circuit 52 operates the aperture 51 to open. By changing the irradiation strength of the light to be irradiated to the living-body tissue, an automatic dimming operation is performed by controlling the aperture 51 such that the brightness of the monitor 6 can agree with the target value.

Here, since the reflected light of the narrow-band light is weaker than that of normal light, the sensitivity multiplication factor of about 30 is required for obtaining the sufficient brightness of the monitor 6 in order to perform narrow-band light observation on the living-body tissue at a far point. Since the intensity signal corrected by the metering correcting circuit 37 is very small, the aperture 51 is controlled to open and is held at the full-open position. The sensitivity control circuit 32 compares the brightness target value of the monitor 6 with the intensity signal. In accordance with the comparison result, the sensitivity control circuit 32 controls the CCD driver circuit 231 to increase or decrease the voltage value (multiplicity) of the sensitivity control pulse φCMD. Thus, the sensitivity multiplication factor of the CCD 19 is increased or decreased, and the intensity signal is changed thereby. Therefore, the intensity signal is controlled to agree with the brightness target value. In this case, an automatic dimming operation is performed only by using the sensitivity multiplication factor of the charge multiplying detector 64 (see FIG. 2) of the CCD 19 (that is, a dimming operation is performed under the control on a priority basis based on the sensitivity multiplication factor of the charge multiplying detector 64).

When a living-body tissue is observed under narrow-band light at a near point and the strength of light entering the CCD 19 is increased to a normal light level, the sensitivity multiplication for the CCD 19 is not required. Thus, the sensitivity multiplication factor output from the CCD driver circuit 231 to the metering correcting circuit 37 is 1. Then, the metering correcting circuit 37 divides the intensity signal by the sensitivity multiplication factor of 1. The metering correcting circuit 37 outputs the same value as the value output from the metering circuit 36 to the aperture control circuit 52.

The aperture control circuit 52 compares the intensity signal with a brightness target value selected by an operator via the brightness control switch 59. Then, in accordance with the comparison result, the aperture control circuit 52 controls the opening/closing of the aperture 51. The aperture control circuit 52 causes the aperture 51 to close if the intensity signal is brighter than the target value. The aperture control circuit 52 causes the aperture 51 to open if the intensity signal is darker than the target value. In this case, an automatic dimming operation is performed only by using the aperture 51 (that is, a dimming operation under the control on a priority basis based on the opening/closing operation of the aperture 51 of the light source apparatus 205).

When a living-body tissue is observed under narrow-band light at a near point and the strength of light entering the CCD 19 is lower than that of the normal light, the condition with the sensitivity multiplication factor of 1 to 2 occurs, which increases the intensity signal corrected by the metering correcting circuit 37. Thus, in the aperture control circuit 52, the brightness target value selected by the operator via the brightness control switch 59 has the same level as the level of the corrected intensity signal.

Thus, when the strength of the light entering the CCD 19 increases, the sensitivity multiplication factor of the CCD 19 gradually decreases. In connection with the gradual decrease in sensitivity multiplication factor of the CCD 19, the aperture 51 operates to close gradually.

When the strength of the light entering the CCD 19 varies to a lower level, the aperture 51 operates to open gradually. In connection with the operation to gradually open, the sensitivity multiplication factor is controlled to gradually increase. In this case, in connection with the sensitivity multiplication factor of the charge multiplying detector 64 (see FIG. 2) and the opening/closing of the aperture 51, an automatic dimming operation is performed at the same time (that is, a dimming operation under the control in connection with the sensitivity multiplication factor of the CCD and the aperture opening/closing operation of the light source apparatus).

Figure 20:
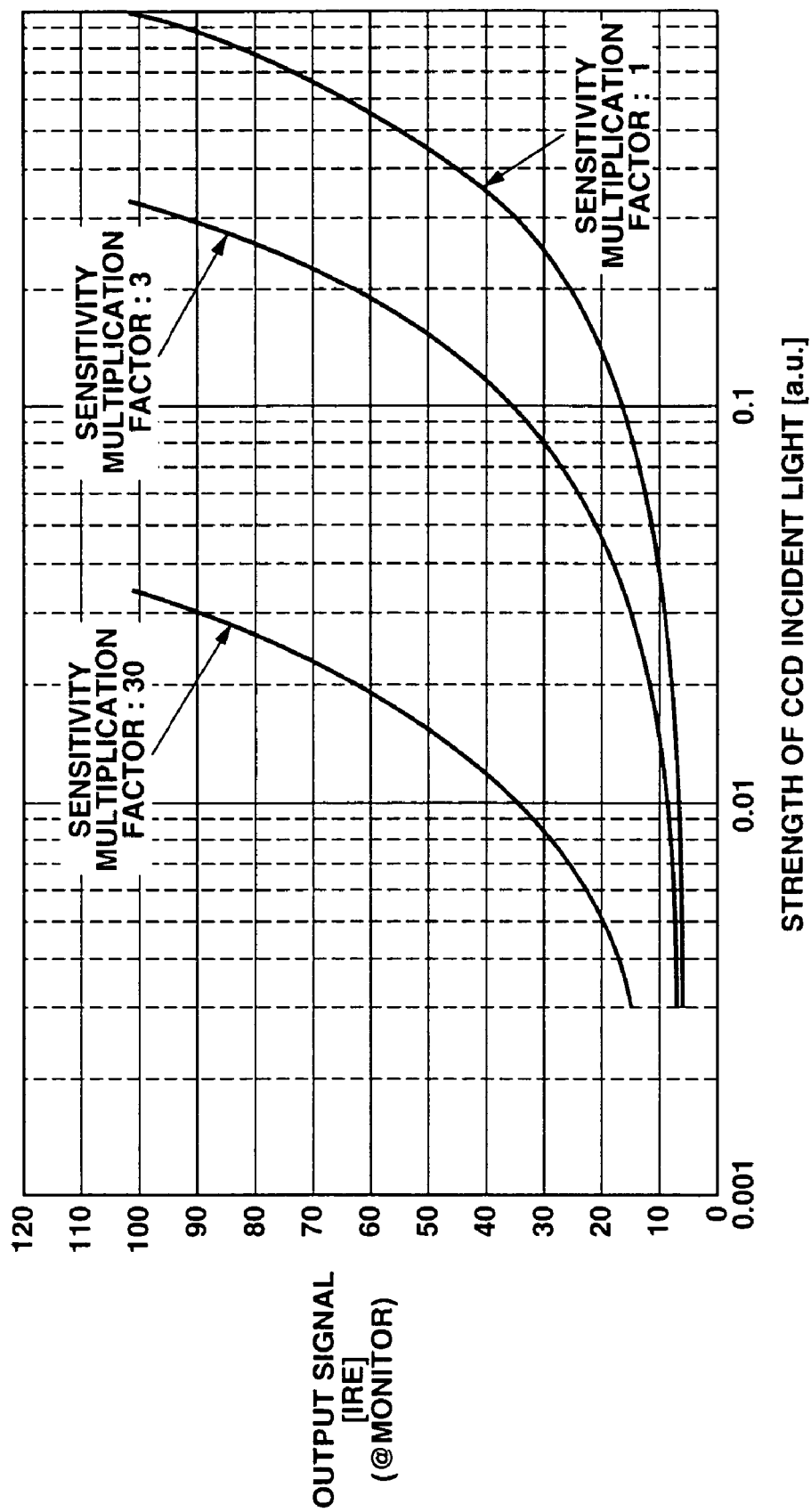
Figure 21:
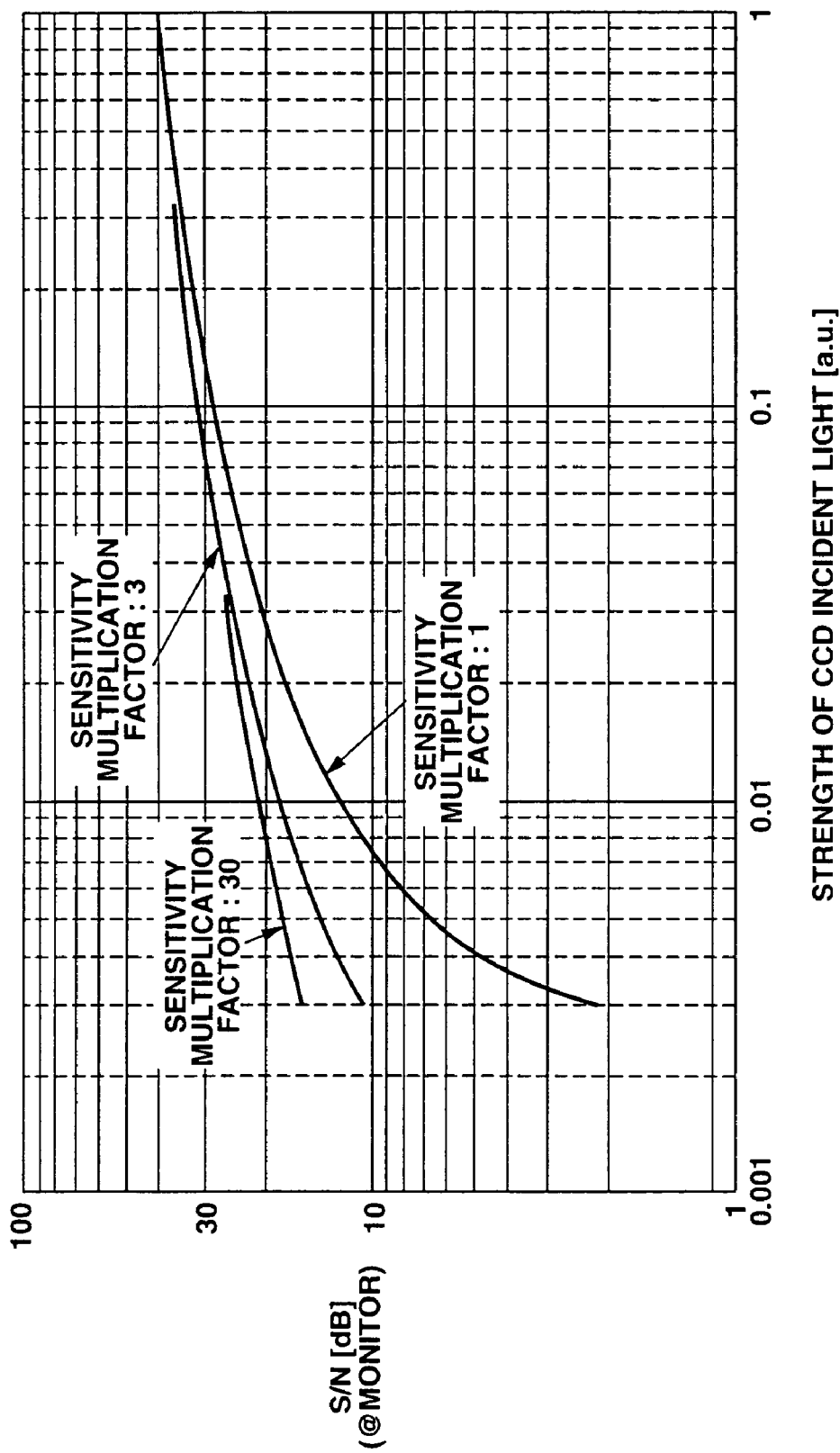

The output signals to be displayed on the monitor 6 and the S/N characteristic are indicated by solid lines in FIGS. 20 and 21. In the narrow-band light region (in the vicinity of a part where the strength of CCD incident light is 0.01 to 0.1 [a.u.] in FIGS. 20 and 21), the higher sensitivity multiplication factor of the CCD 19 than that of the normal light mode can provide the output signals and S/N characteristic by the sensitivity multiplication factor of 1, 3, 30 and so on. With the sensitivity multiplication factor of 1 in a narrow-band light region, the monitor screen is darker and the S/N characteristic is significantly poor. However, by increasing the sensitivity multiplication factor to several times or several tens of times, the brightness of the monitor screen can be increased and a narrow-band light image with a high S/N characteristic (high image quality) can be obtained. Here, any sensitivity multiplication factor can be selected by controlling the applied voltage value (multiplicity).

The narrow-band light observation can more sharply capture the microstructure and/or capillary vessel image of a surface layer (shallow layer) of a mucous membrane of the digestive tract, for example, than the normal light observation by irradiating narrow-band light having a wavelength band especially limited in the blue range (short wavelength side) to a living-body tissue.

The depth of invasion of the light to a mucous membrane in the depth direction depends on the wavelength. As the wavelength decreases, the depth of invasion decreases (the depth decreases) due to the influence of scattering. Furthermore, a mucous membrane (that is, a biological mucous membrane) has a large absorbing band of hemoglobin in the vicinity of 415 nm. Thus, by irradiating narrow-band light especially in the vicinity of 400 to 450 nm, the microstructure and capillary vessel of the mucous membrane surface layer can be detected uniquely. In addition, by using narrow-band light observation, a structure of a mucous membrane surface layer and/or a running pattern of capillary vessels, which are significantly difficult to observe by the normal light observation, can be rendered very clearly. By observing a microstructure of a mucous membrane surface layer and/or a running pattern of capillary vessels in detail by performing an observation under magnification, for example, diagnoses regarding the discrimination of the presence of tumor, benign tumor/malignant tumor and so on can be performed easily.

[Advantages]

According to the third embodiment, the dimming control is properly linked with the sensitivity multiplication factor of the sensitivity adjustable CCD 19 and the opening/closing control of the aperture 51 of the light source apparatus 205 in a special light mode (that is especially for narrow-band light observation here). Thus, a narrow-band light image with proper brightness and high quality can be obtained by preventing the saturation of the image even when the strength of incident light to the CCD 19 largely changes.

Fourth Embodiment

Figure 22:
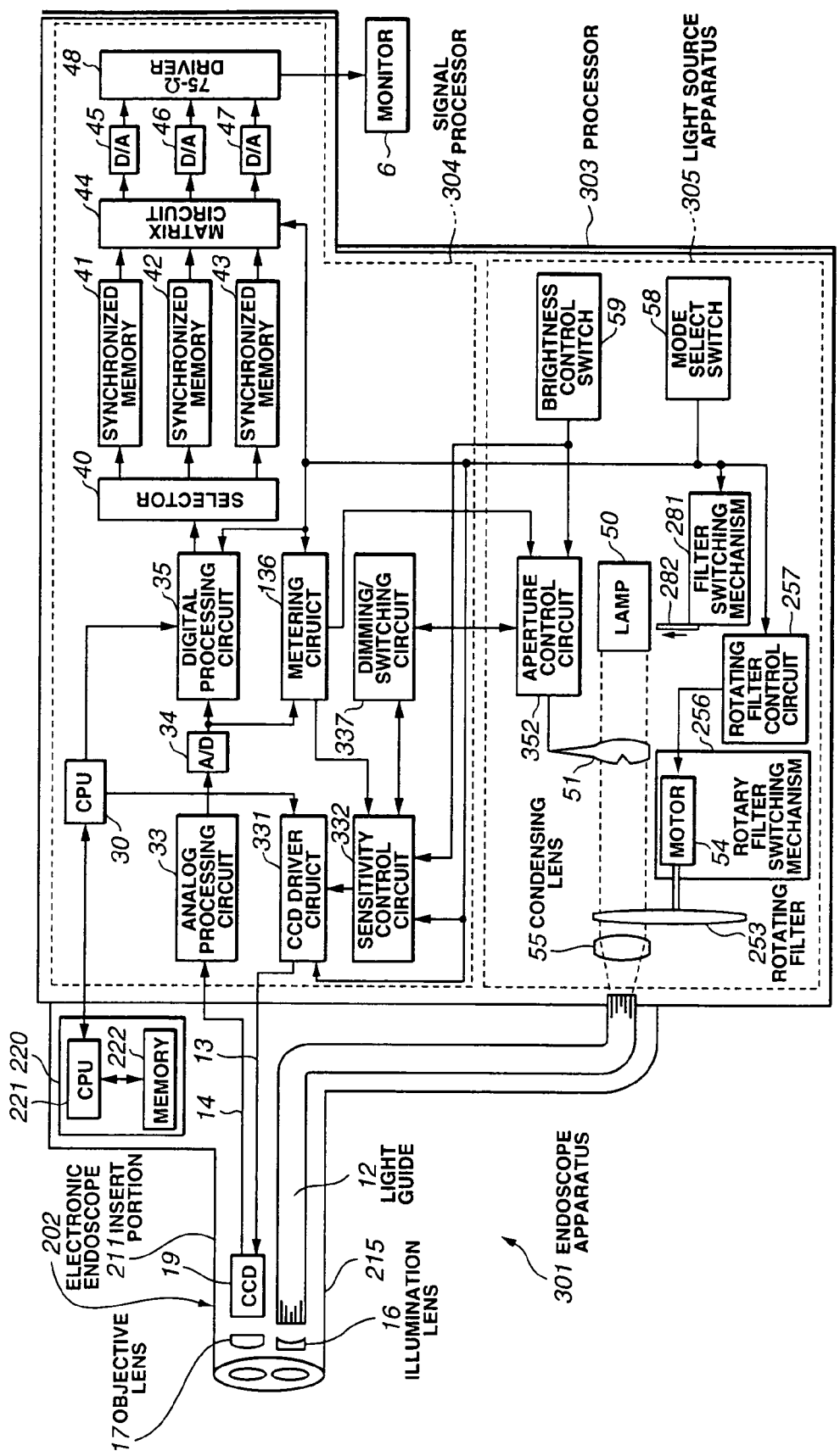
FIGS. 22 and 23 relate to a fourth embodiment of the present invention.
Figure 23:
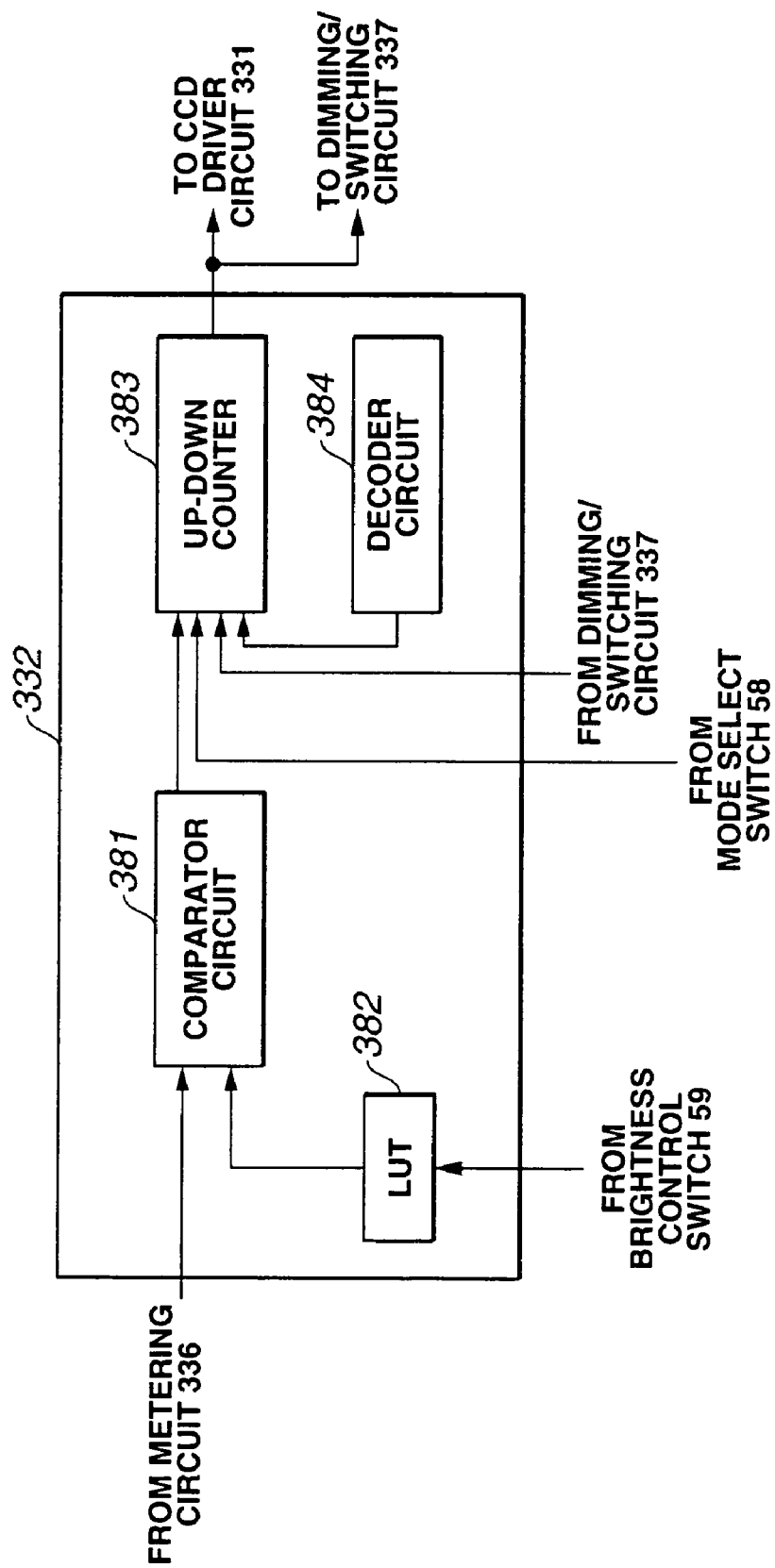

In the description of a fourth embodiment with reference to FIGS. 22 and 23, the same reference numerals are given to the same components as those of the third embodiment shown in FIGS. 16 to 21. Furthermore, the descriptions of the same components will be omitted here.

[Construction]

According to the third embodiment shown in FIGS. 16 to 21, the sensitivity multiplication factor of a sensitivity adjustable CCD and the aperture of a light source are connected during a dimming operation in a special light mode. On the other hand, an endoscope apparatus 301 according to the fourth embodiment has a dimming/switching circuit 337. Here, a dimming operation is performed either by adjusting the sensitivity multiplication factor of the CCD 19 or by performing the aperture opening/closing operation.

As shown in FIG. 22, the endoscope apparatus 301 according to the fourth embodiment has an endoscope 202, a processor 303 and a monitor 6.

The endoscope 202 is removably connected to the processor 303. The processor 303 contains a signal processor 304 and a light source apparatus 305. The light source apparatus 305 may be provided separately from the processor 303.

The monitor 6 is connected to the processor 303 and displays video signals image-processed by the processor 303.

According to this embodiment, the signal processor 304 has a CPU 30, a CCD driver circuit 331, a sensitivity control circuit 332, an analog processing circuit 33, an A/D converter 34, a digital processing circuit 35, a metering circuit 336, a dimming/switching circuit 337, a selector 40, simultaneous memories 41, 42 and 43, a matrix circuit 44, D/A converters 45, 46 and 47 and a 75-Ω driver 48.

The light source apparatus 305 has a lamp 50, an aperture 51, an aperture control circuit 352, a rotating filter 253, a motor 54, a condensing lens 55, a rotating filter switching mechanism 256, a rotating filter control circuit 257, a mode select switch 58, a brightness control switch 59, a filter switching mechanism 281 and an option filter 282.

Operations (light-exposure and light-shield) of the rotating filter 253 in the normal light mode and in a special light (narrow-band light observation) mode, timing of a drive signal supplied by the CCD driver circuit 331 to the CCD 19 and timing of a signal output from the CCD 19 are the same as those of the third embodiment shown in FIGS. 17A to 21.

Counter values Cmin to Cmax are input from the sensitivity control circuit 332 to the CCD driver circuit 331.

The counter values Cmin to Cmax relate to a voltage value of the sensitivity control pulse φCMD output from the sensitivity control circuit 332 to the charge multiplying detector 64 (see FIG. 2) of the CCD 19.

Data of a sensitivity multiplication factor characteristic (that is, a relationship between applied voltage and the sensitivity multiplication factor) of the charge multiplying detector 64 (see FIG. 2) of the CCD 19 is input from a memory 222 to the CCD driver circuit 331 through the CPU 221 and the CPU 30.

The correspondence between the counter values Cmin to Cmax and voltage values Vth to Vmax (see FIG. 4) of voltage to be applied to the charge multiplying detector 64 (see FIG. 2) is defined like the second embodiment such that the voltage Vth is provided when the counter value is the minimum Cmin while the voltage Vmax is provided when the counter value is the maximum Cmax.

The CCD driver circuit 331 outputs the sensitivity control pulse φCMD in the range from Vth to Vmax corresponding to the counter values Cmin to Cmax to the charge multiplying detector 64 (see FIG. 2) of the CCD 19.

The CCD driver circuit 331 corrects such that the minimum value Vth and maximum value Vmax of the sensitivity control pulse φCMD voltage can agree with the minimum Cmin and maximum Cmax of the counter values.

A relationship between a voltage value of the sensitivity control pulse φCMD to be supplied to the charge multiplying detector 64 (see FIG. 2) and the sensitivity multiplication factor according to the fourth embodiment is the same as that of the third embodiment.

Unlike the third embodiment, the metering circuit 336 according to the fourth embodiment outputs an intensity signal calculated for each observation mode to the sensitivity control circuit 332 and the aperture control circuit 352.

As shown in FIG. 23, the sensitivity control circuit 332 has a comparator circuit 381, an LUT circuit 382, an up-down counter 383 and a decoder circuit 384.

The up-down counter 383 counts up or down the counter value between Cmin and Cmax (where C'=C±1) based on a result from a comparison between an intensity signal input from the comparator circuit 381 and a brightness target value.

The up-down counter 383 outputs the counter value to the CCD driver circuit 331, the dimming/switching circuit 337 and the decoder circuit 384. The up-down counter 383 stops the counter output at the maximum value Cmax when a stop signal is input from the decoder circuit 384. Furthermore, the up-down counter 383 sets the counter value at the minimum value Cmin when a mode select signal from the mode select switch 58 is the normal light mode. Thus, the counter operation is stopped. In other words, the sensitivity control circuit 332 operates only in special light modes.

The decoder circuit 384 judges whether or not the counter value input from the up-down counter 383 overflows from the counter value from Cmin to Cmax (refer to the description of the second embodiment). If so, the decoder circuit 384 outputs a stop signal to the up-down counter 383.

The dimming/switching circuit 337 selects one of a dimming permit signal and a dimming stop signal and inputs the selected signal to the up-down counter 383. The up-down counter 383 starts a count operation in response to the input of the dimming permit signal and stops the count operation at the counter value Cmin in response to the input of the dimming stop signal.

In the light source apparatus 305 according to the fourth embodiment, the aperture control circuit 352 is the only different component from the light source apparatus 205 of the third embodiment.

An intensity signal is input from the metering circuit 336 to the aperture control circuit 352. The aperture control circuit 352 compares the intensity signal with a brightness target value selected by an operator via the brightness control switch 59. Based on the comparison result, the aperture control circuit 352 controls the opening/closing of the aperture 51 provided on the optical path between the lamp 50 and the rotating filter 253 and controls an amount of illumination light to be irradiated to the back end surface of the light guide 12.

A dimming permit signal or a dimming stop signal is input from the dimming/switching circuit 337 to the aperture control circuit 352. The aperture control circuit 352 starts controlling the opening/closing of the aperture 51 in response to the input of the dimming permit signal and fixes (or holds) the aperture 51 at a predetermined position (refer to the description of the second embodiment) in response to the input of the dimming stop signal.

The processor 303 can dim by two ways of adjusting the sensitivity multiplication factor of the CCD 19 and performing an opening/closing operation on the aperture 51 of the light source apparatus 305. The dimming/switching circuit 337 determines and selects one of the two dimming ways.

Counter values Cmin to Cmax showing the sensitivity multiplication factors are input from the sensitivity control circuit 332 to the dimming/switching circuit 337. When the counter value Cmin corresponding to the sensitivity multiplication factor of 1 is input to the dimming/switching circuit 337, the dimming/switching circuit 337 outputs a dimming stop signal to the sensitivity control circuit 332. The dimming/switching circuit 337 outputs a dimming permit signal to the aperture control circuit 352 in synchronization with the output of a dimming stop signal to the sensitivity control circuit 332.

Opening/closing position information of the aperture 51 is input from the aperture control circuit 352 to the dimming/switching circuit 337. When the aperture 51 reaches a predetermined position, the dimming/switching circuit 337 outputs a dimming stop signal to the aperture control circuit 352. The dimming/switching circuit 337 outputs a dimming permit signal to the aperture control circuit 352 in synchronization with the output of a dimming stop signal to the sensitivity control circuit 332.

The dimming/switching circuit 337 does not output a dimming permit signal or a dimming stop signal to both of the sensitivity control circuit 332 and the aperture control circuit 352 but outputs a dimming permit signal to one of the circuits and a dimming stop signal to the other circuit.

[Operation]

A way of using the endoscope apparatus 301 according to the fourth embodiment will be described below.

Dimming during a narrow-band light observation will be described below.

In order to perform a narrow-band light observation, an operator selects a narrow-band light observation mode from multiple observation modes via the mode select switch 58. In synchronization with the selection, the filter switching mechanism 281 operates and the option filter 282 is provided on an illumination light path between the lamp 50 and the light guide 12. The rotating filter switching mechanism 256 does not operate, but the same first filter set of rotating filter 253 as that of the normal light observation is provided on the illumination light path.

In order to observe a living-body tissue in the narrow-band light observation mode, the strength of light entering the CCD 19 varies with the change in state of the living-body tissue and in distance between the living-body tissue and the distal end 215 of the endoscope 202. Thus, the brightness screen average value of the monitor 6 may no longer agree with a target value selected by an operator via the brightness control switch 59.

The metering circuit 336 calculates an intensity signal of a narrow-band light image constructed with three wavelengths of narrow-band light and outputs the intensity signal to the sensitivity control circuit 332 and the aperture control circuit 352.

When a narrow-band light observation is performed on the living-body tissue at a far-point distance and when the strength of light entering the CCD 19 is much smaller than that of the normal light observation, a dimming operation is performed as follows.

The dimming/switching circuit 337 outputs a dimming permit signal to the sensitivity control circuit 332 and outputs a dimming stop signal to the aperture control circuit 352. The sensitivity control circuit 332 causes the comparator circuit 381 to compare a brightness target value selected by an operator via the control switch 59 with the intensity signal. Then, the counter value from Cmin to Cmax counted up or down in accordance with the comparison result is output from the up-down counter 383 to the CCD driver circuit 331 and the dimming/switching circuit 337.

The CCD driver circuit 331 outputs a voltage from Vth to Vmax corresponding to the counted up or down counter value from Cmin to Cmax as the sensitivity control pulse φCMD to be applied to the charge multiplying detector 64 (see FIG. 2).

In accordance with the increase/decrease in the voltage of the sensitivity control pulse φCMD, the sensitivity multiplication factor of the CCD 19 increases or decreases. The sensitivity control circuit 332 changes the intensity signal to compensate an amount of change in strength of light entering the CCD 19 and performs automatic gain control such that the intensity signal can agree with the brightness target value.

Since a dimming stop signal is input from the dimming/switching circuit 337 to the aperture control circuit 352, the aperture control circuit 352 forcefully stops an opening/closing operation of the aperture 51. The aperture 51 is fixed (held) at the predetermined position. Thus, the strength of irradiation to the back end surface of the light guide 12 becomes maximum.

When a narrow-band light observation is performed on a living-body tissue at a near-point distance and when the strength of light entering the CCD 19 is equal to that of the normal light observation, a dimming operation is performed as follows.

In this case, the dimming/switching circuit 337 outputs a dimming permit signal to the aperture control circuit 352 and outputs a dimming stop signal to the sensitivity control circuit 332.

The aperture control circuit 352 compares the intensity signal with a brightness target value selected by an operator via the brightness control switch 59 and controls the opening/closing operation of the aperture 51 in accordance with the comparison result.

If the intensity signal is brighter than the target value, the aperture control circuit 352 causes the aperture 51 to operate to close. If the monitor screen is darker than the target value, the aperture control circuit 352 causes the aperture 51 to operate to open. Thus, the aperture control circuit 352 controls such that the strength of irradiation of illumination light to the living-body tissue can be changed and the brightness of the screen of the monitor 6 can be maintained at the target value selected by the operator.

On the other hand, since a dimming stop signal is input from the dimming/switching circuit 337 to the sensitivity control circuit 332, the up-down counter 383 is forcefully stopped. The counter value Cmin is output to the CCD driver circuit 331 and the dimming/switching circuit 337. The sensitivity multiplication factor of the CCD 19 is fixed at 1.

When a narrow-band light observation is performed on a living-body tissue substantially at a near-point distance and when the strength of light entering the CCD 19 is smaller than that of the normal light observation, a dimming operation is performed as follows.

In this case, the dimming/switching circuit 337 alternately outputs dimming permit signals or dimming stop signals to the aperture control circuit 352 and the sensitivity control circuit 332 in accordance with the state.

When the strength of incident light to the CCD 19 is changed to decrease by the sensitivity multiplication factor of 1 to 2, the voltage value of the sensitivity control pulse φCMD from the CCD driver circuit 331 gradually decreases. In accordance with the gradual decrease in voltage value, the sensitivity multiplication factor of the CCD 19 also decreases, and the sensitivity multiplication factor becomes 1. The counter value output from the up-down counter 383 to the dimming/switching circuit 337 is the minimum counter value Cmin corresponding to the sensitivity multiplication factor of 1. The dimming/switching circuit 337 outputs dimming stop signals to the sensitivity control circuit 332 and stops the operation of the up-down counter 383. Thus, the counter value output to the CCD driver circuit 331 is fixed at the minimum counter value Cmin, and the sensitivity multiplication factor of the CCD 19 is fixed at 1. On the other hand, the dimming/switching circuit 337 outputs a dimming permit signal to the aperture control circuit 352 and permits the opening/closing operation of the aperture 51. Then, the aperture control circuit 352 compares the intensity signal with a brightness target value selected by an operator via the brightness control switch 59 with controls the opening/closing operation of the aperture 51 in accordance with the comparison result.

When the strength of incident light to the CCD 19 is changed to increase while the aperture 51 is operating, the aperture 51 operates to open and reaches a predetermined position. The aperture positional information output from the aperture control circuit 352 to the dimming/switching circuit 337 is the predetermined position. Then, the dimming/switching circuit 337 outputs a dimming stop signal to the aperture control circuit 352, and the opening/closing position of the aperture 51 is fixed at the predetermined position. On the other hand, the dimming/switching circuit 337 outputs a dimming permit signal to the sensitivity control circuit 332 and permits a counter operation of the up-down counter 383. Then, the sensitivity control circuit 332 compares the intensity signal with a brightness target value selected by an operator via the brightness control switch 59. In accordance with the comparison result and by counting up or down the counter value, the voltage value of the sensitivity control pulse φCMD to be output by the CCD driver circuit 331 is increased or decreased. Thus, the sensitivity control circuit 332 controls the sensitivity multiplication factor of the CCD 19 to increase or decrease.

[Advantages]

According to the fourth embodiment, a dimming control is performed on the sensitivity multiplication factor of a sensitivity adjustable CCD 19 and the aperture of a light source separately in a proper manner in a special light mode (narrow-band light observation). Thus, even when the strength of the incident light to the CCD 19 varies largely, the saturation of an image can be prevented. Therefore, the narrow-band light image can have proper brightness and high quality.

[Variation Examples]

(1) According to the first and fourth embodiments, a charge multiplying detector may be provided in each pixel. In this case, charge multiplication can be performed by applying a sensitivity control pulse from a processor to the charge multiplying detector of a CCD. The sensitivity multiplication factor can be adjusted by controlling a voltage value of the sensitivity control pulse and the number of pulses.

(2) According to the first and fourth embodiment, the minimum counter value corresponds to the voltage value (multiplicity) of the sensitivity control pulse by the sensitivity multiplication factor of 1. However, the minimum counter value may correspond to a voltage value (multiplicity) causing a predetermined sensitivity multiplication factor other than the sensitivity multiplication factor of 1 (with no multiplicities).

(3) According to the first to fourth embodiments, a value of voltage to be applied to a charge multiplying detector is ±ΔV(V) linearly in accordance with the change ±1 in counter value, for example. However, a counter value and an amount of change in applied voltage may be nonlinear. Various applications thereof are possible. For example, an area having a lower counter value (that is, an area having a lower sensitivity multiplication factor) may have a large amount of change in applied voltage. On the other hand, an area having a higher counter value (that is, an area having a higher sensitivity multiplication factor) may have a small amount of change in applied voltage.

(4) According to the first to fourth embodiments, a CCD, which is one solid image pickup element, is provided at the distal end of an endoscope, for example. However, two CCDs may be provided at the distal end of an endoscope. Then, a first CCD may be used for the normal light mode while a second CCD may be provided for a special light mode.

In this case, CCD switching means for a CCD drive signal and a read signal, which includes a relay, for example, may be provided within the endoscope or within a cable connecting the endoscope and a processor. Thus, CCDs corresponding to observation modes may be driven and be read out in accordance with a mode select signal from a mode switching circuit.

In this case, for example, multiple signals common to two CCDs may be switched by using multiple mechanical and/or electric relays. Signals which are not common to the two CCDs can be connected between the CCDs and the processor.

Thus, the number of cables connecting the processor and the endoscope may be reduced. Furthermore, CCD driver and readout circuits corresponding to the two CCDs may be provided within the processor. An advantage of the two-CCD type is that better color reproduction can be achieved since an exciting light cut filter is not required in front of the CCD for performing a normal light observation.

(5) According to the first to fourth embodiments, a CCD is provided at the distal end of the endoscope. However, the CCD may be provided outside of a fiber-optic endoscope (at a position other than an insert portion) having an image fiber for transmitting images to the inside of the endoscope. An integral and hybrid type construction and/or removable construction may be adopted. Since a CCD is not required at the distal end of the endoscope, the outer radius of the insert portion may be advantageously reduced.

(6) According to the first to fourth embodiments, a sensitivity adjustable CCD is used for imaging weaker incident light than that of normal light observation. However, in order to image a much higher S/N characteristic, the integrating time may be extended. Furthermore, pixel-binning-reading may be combined thereto for adding surrounding pixels in the CCD, and calculation processing such as adding multiple field images within the processor may be performed.

(7) According to the first to fourth embodiment, data relating to sensitivity multiplication factor characteristics is stored in a storage device disposed in an endoscope. However, data relating to sensitivity multiplication factor characteristics may be stored in a processor.

(8) According to the first and second embodiment, three wavelengths for fluorescence observation are fluorescence, green reflected light and red reflected light. However, various selections and/or combinations of the numbers of wavelengths, wavelength bands, transmittances and so on of exciting light and reflected light can be applied. Alternatively, only fluorescence may be imaged.

(9) According to the first and second embodiments, auto fluorescence and reflected light are used as ones having special wavelengths for fluorescence observation, for example. However, PDD may be combined with reflected light instead of auto fluorescence. In this case, various selections and/or combinations of the numbers of wavelengths, wavelength bands and so on of exciting light and reflected light may be adopted. Alternatively, only PDD may be imaged.

(10) According to the third and fourth embodiments, three wavelengths of narrow-band light are blue, green and red narrow-band light beams. However, various selections and/or combinations of the numbers of wavelengths, the center wavelength and so on of narrow-band bands may be applied by limiting the wavelength bands.

(11) According to the third and fourth embodiments, a filter for generating narrow-band light is provided in an option filter. However, it may be provided in a second filter set of a rotating filter may be provided. In this case, the combination of R, G and B filters for normal light is no longer required. Thus, the degree of freedom for selections and/or combinations of the numbers of wavelengths, the center wavelength and so on for the narrow-band is improved. For example, three wavelengths may be provided in the blue region. Thus, at least one wavelength may be used as narrow-band light. Alternatively, at least one wavelength may be used as the narrow-band in the bands of ultraviolet light to visible light.

(12) According to the first to fourth embodiments, fluorescence observation and narrow-band light observation are described as special light mode examples. However, indocyanine green (ICG) having a strong absorbing band in the vicinity of 800 nm is infused to a living-body tissue. Then, light with multiple wavelengths in a wavelength band in the vicinity of 800 nm (for mainly observing the degree of ICG absorption) and in a wavelength band in the vicinity of 900 nm (functioning as reference light) are irradiated to the living-body tissue. Thus, infrared observation for observing the reflected light is allowed by changing the wavelength characteristics of the filters. Various selections and/or combinations of the numbers of wavelength, wavelength bands and so on of light to be illuminated may be applied for infrared observation.

(13) According to the first to fourth embodiments, the control of the sensitivity multiplication of a solid image pickup element is terminated in the normal light observation mode. However, the control of the sensitivity multiplication of the solid image pickup element can be performed in the normal light observation mode as well as in the special light observation modes.

(14) According to the first to fourth embodiments, a dimming operation is properly combined with the control of a sensitivity multiplication factor of a CCD and an aperture control of a light source. An electronic shutter may be further combined thereto.

(15) According to the first to fourth embodiments, gain values of a preamplifier of the analog processing circuit 33 may be switched in accordance with an observation mode. With this mechanism, a higher gain value of the preamplifier in a special light mode is defined than that of the normal light mode. By switching gain values of the amplifiers in synchronization with a manipulation of the mode select switch 58, a CCD output signal of special light is more largely multiplied than that for normal light.

In this invention, it is apparent that various embodiments can be made without departing from the spirit and scope of the invention. It is to be understood that the invention is not limited to the specific embodiments thereof except as defined in the appended claims.

What is claimed is:

1. An endoscope apparatus, comprising:
    an endoscope having an image pickup element having a sensitivity, which can be changed by multiplying generated charges by supplied pulse-type signals;
    a light source portion for irradiating light to an object;
    an aperture portion for adjusting an amount of light to be irradiated to the object;
    a driver portion for adjusting and supplying the pulse-type signals to the image pickup element in order to change the sensitivity of the image pickup element;
    a metering portion for generating an intensity signal based on a signal output from the image pickup element;
    a sensitivity control portion for, based on the intensity signal of the metering portion, supplying to the driver portion a sensitivity control signal for generating the pulse-type signals for controlling a charge multiplication factor of the image pickup element;
    an aperture control portion for controlling the aperture portion based on the intensity signal of the metering portion; and
    a dimming/switching portion for selectively operating sensitivity control of the image pickup element by the sensitivity control portion and the aperture portion by the aperture control portion in accordance with intensity of the intensity signals,
    wherein, in a state where the sensitivity control of the image pickup element by the sensitivity control portion is operated, when the intensity of the intensity signal is equal to or greater than a predetermined value and a sensitivity multiplication factor is the predetermined minimum value, the dimming/switching portion fixes the sensitivity multiplication factor to the predetermined minimum value and operates only the control of the aperture portion by the aperture control portion, and
    in a state where the control of the aperture portion by the aperture control portion is operated, when the intensity of the intensity signal is smaller than the predetermined value and the aperture portion is at a full-open position, the dimming/switching portion fixes the aperture portion at the full-open position and operates only the sensitivity control of the image pickup element by the sensitivity control portion.

2. An endoscope apparatus according to claim 1, wherein the image pickup element has a charge multiplying detector for adjusting a sensitivity by multiplying generated charges by controlling the multiplicity of the pulse-type signals or the number of pulses when ionizing occurs due to the supplied pulse-type signals.

3. An endoscope apparatus according to claim 2, wherein the charge multiplying detector is provided between a horizontal transfer register and a floating diffusion amplifier or in each pixel.

4. An endoscope apparatus according to claim 1,
    wherein the light source portion can switch and irradiate a normal light beam for performing normal light observation and multiple special light beams for performing special light observation.

5. An endoscope apparatus according to claim 4,
    wherein the signal processing portion has a mode switching portion for switching a normal light mode for performing the normal light observation and a special light mode for performing the special light observation.

6. An endoscope apparatus according to claim 5,
    wherein the multiple special light beams are an exciting light beam for fluorescence and an illumination light beam for reflected light, and the special light mode is a fluorescence observation mode.

7. An endoscope apparatus according to claim 5,
    wherein the multiple special light beams arc illumination light beams in the near-infrared region, and the special light mode is an infrared observation mode.

8. An endoscope apparatus according to claim 5,
    wherein the multiple special light beams are a blue exciting light beam for fluorescence and illumination light beams in the green and red regions for reflected light, and the special light mode is a fluorescence observation mode.

9. An endoscope apparatus according to claim 5,
    wherein the multiple special light beams are an exciting light beam for fluorescence and an illumination light beam for reflected light, and the special light mode is a PDD observation mode.

10. An endoscope apparatus according to claim 1,
    wherein the predetermined minimum value of the sensitivity multiplication factor is 1.

* * * * *